United States Patent [19]
Wakabayashi et al.

[11] Patent Number: 5,789,423
[45] Date of Patent: Aug. 4, 1998

[54] 3-[(5-SUBSTITUTED BENZYL)AMINO]-2-PHENYLPIPERIDINES AS SUBSTANCE P ANTAGONISTS

[75] Inventors: Hiroaki Wakabayashi, Kariya; Yuji Shishido, Aichi-ken, both of Japan

[73] Assignee: Pfizer Inc., New York, N.Y.

[21] Appl. No.: 767,985

[22] Filed: Dec. 17, 1996

[30] Foreign Application Priority Data

Dec. 21, 1995 [WO] WIPO ............ PCT/IB95/01148

[51] Int. Cl.⁶ .................................................. A61K 31/445
[52] U.S. Cl. ................................. 514/329; 546/223
[58] Field of Search .......................... 546/223; 514/329

[56] References Cited

U.S. PATENT DOCUMENTS 5,232,929  8/1993  Desai et al. ............................ 514/314

OTHER PUBLICATIONS

Couture et al. "Characterization of the tachykinin receptors involved . . ." CA 124:833, 1995.
Maggi et al. "Tachykinin receptors and tachykini . . ." J. Autom. Pharmac. v.13, pp. 23–24, 1993.
Webster's II dictionary, p. 1173, 1984.

*Primary Examiner*—Ceila Chang
*Attorney, Agent, or Firm*—Peter C. Richardson; Paul H. Ginsburg; B. Timothy Creagan

[57] ABSTRACT

This invention provides a compound of the formula:

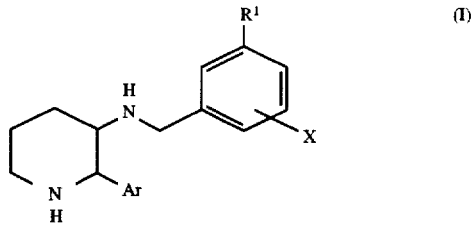

and its pharmaceutically acceptable salts, wherein
$R^1$ is $C_1-C_6$ alkyl, $C_3-C_6$ cycloalkyl, halo $C_1-C_6$ alkyl or terahydropyranyl, having one or more substituents selected from cyano, 1,3-thiazolanyl, $COOR^2$, $COR^2$, $OCOR^2$, $CONR^3R^4$, $NR^3R^4$, $NR^5COR^3$ and $C\equiv CR^6$, wherein $R^2$ is hydrogen or $C_1-C_4$ alkyl, $R^3$ and $R^4$ are independently hydrogen, $C_1-C_4$ alkyl or $C_3-C_6$ cycloalkyl, $R^5$ is $C_1-C_4$ alkyl or $C_3-C_6$ cycloalkyl and $R^6$ is hydrogen, halo, cyano, $C_1-C_6$ alkyl, COOH, $COO(C_1-C_4$ alkyl) or phenyl; X is $C_1-C_6$ alkoxy or halo $C_1-C_6$ alkoxy; and Ar is phenyl optionally substituted with halo.

These compounds are useful in the treatment of allergic disorders, angiogenesis, gastrointestinal disorders, central nervous system disorders, inflammatory diseases, emesis, urinary incontinence, pain, migraine, sunburn, and diseases, disorders and adverse conditions caused by *Helicobacter pylori*, in a mammalian subject.

8 Claims, No Drawings

3-[(5-SUBSTITUTED BENZYL)AMINO]-2-PHENYLPIPERIDINES AS SUBSTANCE P ANTAGONISTS

TECHNICAL FIELD

This invention relates to substituted 3-[(5-substituted benzyl)amino]-2-phenylpiperidine compounds and their pharmaceutically acceptable salts, pharmaceutical compositions containing such compounds, and use of such compounds as substance P antagonists.

BACKGROUND ART

Substance P is a naturally occurring undecapeptide belonging to the tachykinin family of peptides, the latter being so-named because of their prompt stimulatory action on smooth muscle tissue. More specifically, substance P is a pharmaceutically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine, as well as in central nervous system disorders such as anxiety and schizophrenia, in respiratory and inflammatory diseases such as asthma and rheumatoid arthritis, respectively, and in gastrointestinal disorders and diseases of GI tract, like ulcerative colitis and Crohn's diseases, etc. It is also reported that the tachykinin antagonists are useful for the treatment of allergic conditions, immunoregulation, vasodilation, bronchospasm, reflex or neuronal control of the viscera and senile dementia of the Alzheimer type, emesis, sunburn and *Helicobacter pylori* infection.

International Publication No. WO 93/01170, WO93/00331, WO93/11110 and WO 94/26740 disclose a wide variety of piperidine and quinuclidine derivatives, as tachykinin antagonists such as substance P antagonists.

BRIEF DESCRIPTION OF THE INVENTION

The present invention provides substituted piperidine compounds of the following chemical formula (I):

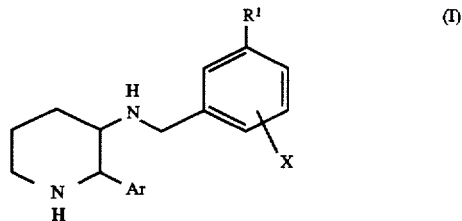

(I)

and its pharmaceutically acceptable salts, wherein $R^1$ is $C_1$–$C_6$ alkyl, $C_3$–$C_6$ cycloalkyl, halo $C_1$–$C_6$ alkyl or terahydropyranyl, having one or more (preferably one or two) substituents selected from cyano, 1,3-thiazolanyl, $COOR^2$, $COR^2$, $OCOR^2$, $CONR^3R^4$, $NR^3R^4$, $NR^5COR^3$ and $C\equiv CR^6$, wherein $R^2$ is hydrogen or $C_1$–$C_4$ alkyl, $R^3$ and $R^4$ are independently hydrogen, $C_1$–$C_4$ alkyl or $C_3$–$C_6$ cycloalkyl, $R^5$ is $C_1$–$C_4$ alkyl or $C_3$–$C_6$ cycloalkyl and $R^6$ is hydrogen, halo, cyano, $C_1$–$C_6$ alkyl, COOH, COO($C_1$–$C_4$ alkyl) or phenyl;

X is $C_1$–$C_6$ alkoxy or halo $C_1$–$C_6$ alkoxy; and

Ar is phenyl optionally substituted with halo.

These compounds are useful as substance P antagonists, and thus useful as analgesics or anti-inflammatory agents, or in the treatment of allergic disorders, angiogenesis, central nervous system (CNS) disorders, emesis, gastrointestinal disorders, sunburn, urinary incontinence, diseases, disorders or adverse conditions caused by *Helicobacter pylori*, or the like, in a mammalian subject, especially human. These compounds are especially useful as analgesics or anti-inflammatory agents in the periphery, and/or useful in the treatment of CNS disorders, in the subject.

Accordingly, the present invention provides a pharmaceutical composition for the prevention or treatment of a medical condition for which antagonist activity toward substance P is needed, in a mammalian subject, which comprises the compound of the formula (I) or a pharmaceutically acceptable salt thereof, and a pharmaceutically acceptable carrier. The medical condition includes allergic disorders, angiogenesis, gastrointestinal disorders, CNS disorders, inflammatory diseases, emesis, urinary incontinence, pain, migraine, sunburn, and diseases, disorders, disorders and adverse conditions caused by *Helicobacter pylori*, in a mammalian subject.

The present invention also provides a method for the prevention or treatment of a medical condition for which antagonist activity toward substance P is needed, in a mammalian subject, which comprises administering to said subject a compound of the formula (I) or a pharmaceutically acceptable salt thereof.

DETAILED DESCRIPTION OF THE INVENTION

In this specification, the term "$C_3$–$C_6$ cycloalkyl" is used to mean cyclic alkyl of 3 to 6 carbon atoms including, but not limited to, cyclopropyl, cyclobutyl, cyclopentyl, cyclohexyl and the like.

The term "halo $C_1$–$C_6$ alkyl" is used herein to mean a straight or branched halo alkyl of 1 to 6 carbon atoms including, but not limited to, methyl, ethyl, n-propyl, isopropyl, n-butyl, sec-butyl and tert-butyl, substituted with 1 to 13 (preferably 1 to 6) halogen atoms.

The term "halo" means F, Cl, Br, and I preferably Cl or F.

Preferably $R^1$ is $C_1$–$C_6$ alkyl, $C_3$–$C_6$ cycloalkyl, halo $C_1$–$C_6$ alkyl or terahydropyranyl, having one or more substituents selected from cyano, 1,3-thiazolanyl, $COOR^2$, $COR^2$, $NR^5COR^3$ and $C\equiv CR^6$, wherein $R^2$, $R^3$ and $R^5$ are independently $C_1$–$C_4$ alkyl and $R^6$ is hydrogen, cyano, $C_1$–$C_4$ alkyl, COO($C_1$–$C_4$ alkyl) or phenyl. More preferably $R^1$ is $C_1$–$C_4$ alkyl, cyclopropyl or halo $C_1$–$C_4$ alkyl, substituted with cyano, $C\equiv CH$ or $COCH_3$.

Preferably X is methoxy or isopropoxy, more preferably X is methoxy, and is at 2-position on the phenyl ring. Preferably Ar is phenyl.

In these compounds, the preferable stereochemistry of 2-aryl and 3-benzylamino is (2S, 3S).

Especially preferred individual compounds of the invention include:

(2S,3S)-3-(5-(1-cyanocyclopropyl)-2-methoxybenzyl)amino-2-phenylpiperidine dihydrochloride or its salts;

(2S,3S)-3-(5-(1-cyanoethyl)-2-methoxybenzyl)amino-2-phenyl-1-piperidine or its salts;

(2S,3S)-3-(2-methoxy-5-(1,1-dimethyl-2-propynyl)benzyl)amino-2-phenylpiperidine or its salts;

(2S,3S)-3-(5-(1-cyano-1-methylethyl)-2-methoxybenzyl)amino-2-phenylpiperidine or its salts;

(2S,3S)-3-(5-(1,1-dicyanoethyl)-2-methoxybenzyl)amino-2-phenylpiperidin or its salts;

(2S,3S)-3-(5-(1-cyano-1-methylethyl)-2-isopropoxybenzyl)amino-2-phenylpiperidine or its salts;

(2S,3S)-3-(5-(2-cyano-1,1-dimethylethyl)-2-methoxybenzyl)amino-2-phenylpiperidine or its salts;

(2S,3S)-3-(5-cyanomethyl-2-methoxybenzyl)amino-2-phenylpiperidine or its salts;

(2S,3S)-3-[5-(2-propynyl)-2-methoxybenzyl]amino-2-phenylpiperidine or its salts;

(2S,3S)-3-(2-methoxy-5-(2-methyl-3-oxo-butan-2-yl)-benzyl)amino-2-phenylpiperidine or its salts; and (2S,3S)-3-(5-(1-cyano-2,2,2-trifluoro-1-methylethyl)-2-methoxybenzyl)amino-2-phenylpiperidine or its salts.

General Synthesis

The piperidine compounds of the formula (I) of this invention may be prepared as described in the following reaction schemes.

Unless otherwise indicated, in the reaction schemes that follow, $R^1$, X and Ar are defined as above.

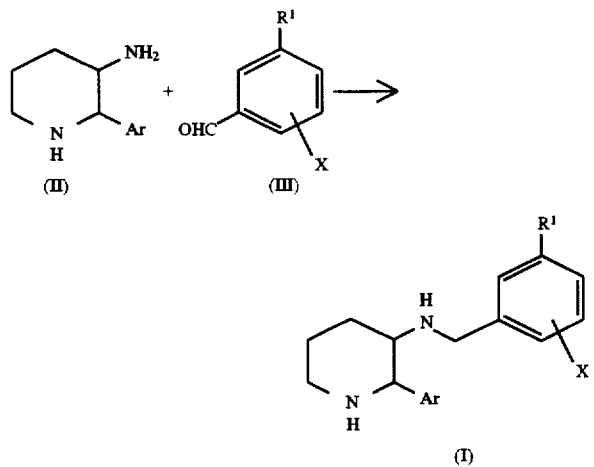

Scheme A-I illustrates a method for preparing compounds of the formula (I) by reductive amination of a compound of the formula (III) with a compound (II). The reduction can be carried out by catalytic hydrogenation, or with several hydride reagents in a reaction-inert solvent. The catalytic hydrogenation may be carried out in the presence of a metal catalyst such as palladium or Raney nickel. Suitable hydride reagents include borohydrides such as sodium borohydride ($NaBH_4$), sodium cyanoborohydride ($NaBH_3CN$) and sodium triacetoxyborohydride ($NaB(OAc)_3H$), boranes, aluminum-based reagents and trialkylsilanes. Suitable solvents include polar solvents such as methanol, ethanol, methylene chloride, tetrahydrofuran (THF), dioxane and ethylacteate. This reaction is typically carried out at a temperature from −78° C. to reflux temperature of the solvent, preferably from 0° C. to 25° C. for 5 minutes to 48 hours, preferably from 0.5 to 12 hours.

Alternatively, the piperidine compounds of the formula (I) of this invention may be prepared as shown in the following scheme A-II.

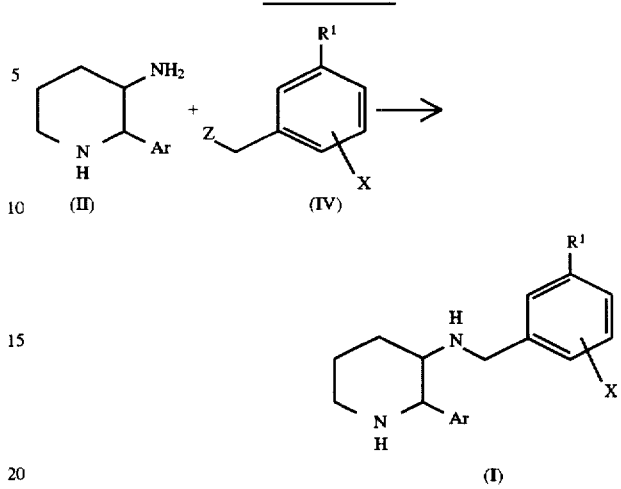

(wherein Z is a leaving group such as halo or sulfonate including tosylate or mesylate)

Referring to Scheme A-II, the compounds of the formula (I) of this invention may be prepared by a reaction of a compound of the formula (IV) with a compound (II). The compound (IV) may be treated with compound (II) in the presence of a base (e.g., $K_2CO_3$ or $Na_2CO_3$) in a polar solvent (e.g., methanol, ethanol, isopropylalcohol, THF, dioxane, dimethylformamide (DMF) or dimethylsulfoxide (DMSO)). This reaction is typically carried out at a temperature from −78° C. to reflux temperature of the solvent, preferably from 0° C. to 25° C. for 5 minutes to 48 hours, preferably from 0.5 to 12 hours.

The compounds (IV) may be prepared by reduction of an aldehyde of the formula (III), followed by conversion of a hydroxy group of the resultant compound into a leaving group, Z. Reduction of the aldehyde (III) may be accomplished using a variety of reducing agents in a reaction-inert solvent. Suitable reducing agent/solvent systems include sodium tetrahydroborate ($NaBH_4$) in methanol or ethanol; lithium tetrahydroborate ($LiBH_4$) in THF or diethyl ether; lithium tetrahydroaluminum ($LiAlH_4$), lithium triethoxyhydroaluminum ($LiAl(OEt)_3H$) lithium tert-buthoxyhydroaluminum ($LiAl(OBut)_3H$) or aluminum trihydride ($AlH_3$) in THF or diethyl ether; and iso-butyl aluminum hydride(i-$BuAlH_2$) or diisopropyl aluminum hydride (DIBAL-H) in dichloromethane, THF or n-hexane. This reaction is generally carried out at a temperature from −20° C. to 25° C. for 5 minutes to 12 hours. Then, the hydroxy group of the resultant compound is converted to a leaving group, Z (e.g., halo such as chloro, bromo, iodo or fluoro, or sulfonate including tosylate or mesylate). Conversion of the hydroxy group into the leaving group, Z may be accomplished according to methods known to those skilled in the art. For example, when Z is sulfonate such as tosylate or mesylate, the hydroxy compound is reacted with sulfonate in the presence of pyridine or triethylamine in dichloromethane. When Z is halo such as chloro or bromo, the hydroxy compound may be treated with $SOX_2$ (X is Cl or Br) in the presence of pyridine.

The compounds of the formula (III) can be prepared as illustrated in the following scheme B-I.

Scheme B-I

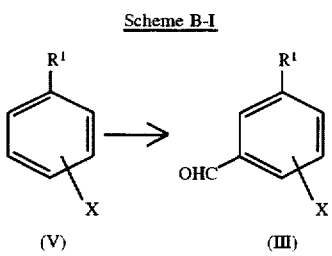

The compounds of the formula (III) may be prepared by direct or indirect formylation of a compound of the formula (V). Any formylation methods known to those skilled in the art may be used, to introduce a formyl group into a benzene ring. For example, direct formylation may be accomplished by contacting the compound (V) with a suitable formylating agent in the presence of a suitable catalyst. Suitable formylating agent/catalyst systems include dichloromethyl methyl ether/titanium (IV) chloride ($Cl_2CHOCH_3/TiCl_4$), trifluoroacetic acid ($CF_3CO_2H$)/hexamethylenetetramine (modified Duff's conditions) and phosphoryl trichloride ($POCl_3$)/DMF (Vilsmeier's conditions). Indirect formylation may be achieved by halogenating the compound (V), displacing the halogen atom introduced with a cyano group, and then subjecting the resultant cyano-substituted compound to reduction. The halogenation as used herein may be carried out according to the procedure reported in G. A. Olah et. al., *J. Org Chem*, Vol. 58, p. 3194, 1993. The displacement of the halogen atom with a cyano group may be performed according to the methods reported in D. M. Tschaem et. al., *Synth Commun*, Vol. 24, p. 887, 1994, K. Takagi et. al., *Bull Chem. Soc. Jpn*. Vol. 64, p. 1118, 1991. The reduction as used herein may be performed in the presence of diisopropyl aluminiumhydride (DIBAL-H) in dichloromethane or Raney nickel in formic acid.

The starting materials of the formula (V) are either known compounds or can be prepared by conventional procedures. For example, compounds of the formula (V) wherein X is alkoxy can be prepared by O-alkylation of the corresponding compounds (V) wherein X is hydroxy, in the presence of a base (e.g., NaH or KH) in a suitable solvent (e.g., DMSO, DMF and THF).

Compound (V) can be also prepared by other methods as described for example in the following literature:

(A) M. Olomucki et. al., *J. Chem. Soc., Chem. Commun.*, pp. 1290–1291, 1982;

(B) R. E. Murray et. al., *Synthesis Communication*, pp. 150–151, February, 1980;

(C) K. Sonogashira et. al., *Tetrahedron Letters*, No. 50, pp. 4467–4470, 1975;

(D) K. Okura et. al., *Tetrahedron Letters*, Vol. 33, No. 37, pp. 5363–5364, 1992; and (E) S. C. Sondej et.al., *J. Org. Chem.* Vol. 51, pp. 3508–3513, 1986.

Alternatively, compounds of the formula (I) may be prepared as shown in the following Scheme A-III.

Scheme A-III

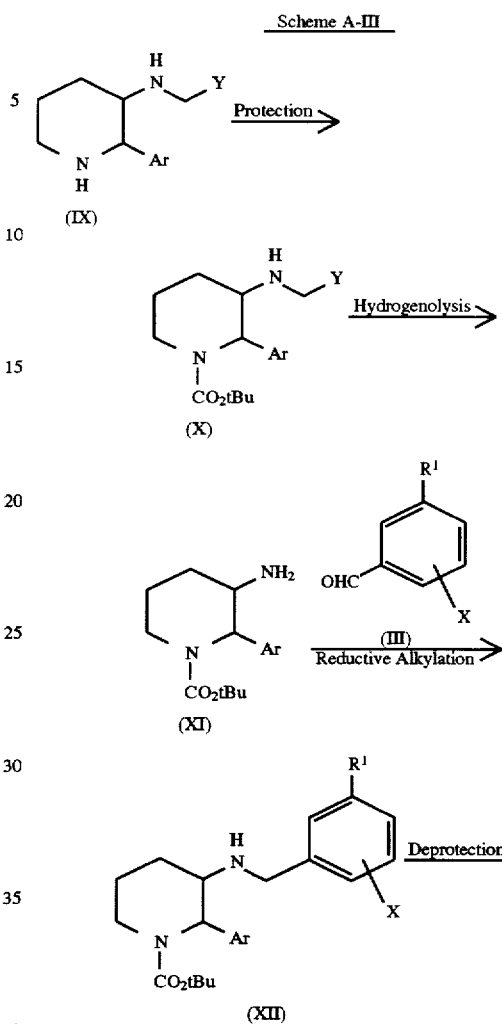

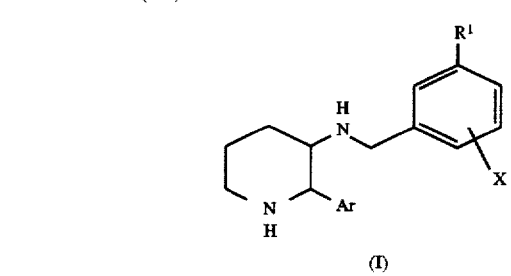

Scheme A-III illustrates the preparation of compounds of the formula (I). Referring to Scheme A-III, N-protection of a compound of the formula (IX) (Ar is phenyl or the like) may be carried out by treatment with (t-BuOCO)$_2$O (Boc$_2$O) in the presence of a base such as sodium bicarbonate (NaHCO$_3$) or triethylamine (Et$_3$N) to obtain a compound of the formula (X). Compound (X) is subjected to hydrogenolysis to obtain a compound of the formula (XI) (wherein Ar is phenyl). An alternative route for N-protection of a compound of the formula (IX) may be carried out by treatment with carbobenzoxy chloride (Cbz-Cl) in the presence of a base such as sodium bicarbonate (NaHCO$_3$) or triethylamine (Et$_3$N), wherein Ar is phenyl. The hydrogenolysis may be carried out by treatment with H$_2$ or ammonium formate (HCO$_2$NH$_4$) in the presence of a metal catalyst such as a palladium on charcoal (e.g. 20% palladium on charcoal) in a suitable solvent. Then, the compound (XI)

is subjected to the reductive amination as described in Scheme A-I. The compound (XII) may be converted into a compound of the formula (I) by treatment with acid catalyst such as hydrochloride (HCl) in methanol, conc.HCl in ethylacetate or $CF_3CO_2H$ in dichloroethane.

The compounds of formula (I), and the intermediates shown in the above reaction schemes can be isolated and purified by conventional procedures, such as recrystallization or chromatographic separation.

As the piperidine compounds of this invention possess at least two asymmetric centers, they are capable of occurring in various stereoisomeric forms or configurations. Hence, the compounds can exist in separated (+)- and (−)-optically active forms, as well as mixtures thereof. The present invention includes all such forms within its scope. Individual isomers can be obtained by known methods, such as optical resolution, optically selective reaction, or chromatographic separation in the preparation of the final product or its intermediate.

In so far as the piperidine compounds of this invention are basic compounds, they are all capable of forming a wide variety of different salts with various inorganic and organic acids. Although such salts must be pharmaceutically acceptable for administration to animals, it is often desirable in practice to initially isolate the piperidine base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the piperidine base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acid which are used to prepare the pharmaceutically acceptable acid addition salts of the aforementioned piperidine base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate))salts.

The piperidine compounds of the invention which have also acidic groups are capable of forming base salts with various pharmaceutically acceptable cations. Examples of such salts include the alkali metal or alkaline-earth metal salts and particularly, the sodium and potassium salts. These salts are all prepared by conventional techniques.

The chemical bases which are used as reagents to prepare the pharmaceutically acceptable base salts of this invention are those which form non-toxic base salts with the herein described acidic piperidine derivatives. These particular non-toxic base salts include those derived form such pharmaceutically acceptable cations as sodium, potassium, calcium and magnesium, etc. These salts can easily be prepared by treating the aforementioned acidic piperidine compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The active piperidine compounds of the present invention exhibit significant substance P receptor-binding activity and therefore, are of value in the treatment of a wide variety of clinical conditions which are characterized by the presence of an excess of said substance P activity. Such conditions include gastrointestinal disorders, central nervous system disorders, inflammatory diseases, emesis, urinary incontinence, pain, migraine or angiogenesis in a mammalian subject, especially humans.

The active piperidine compounds of the formula (I) of this invention can be administered via either the oral, parenteral or topical routes to mammals. In general, these compounds are most desirably administered to humans in doses ranging from about 0.3 mg up to 750 mg per day, although variations will necessarily occur depending upon the weight and condition of the subject being treated and the particular route of administration chosen. However, a dosage level that is in the range of from about 0.06 mg to about 2 mg per kg of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention, as substance P antagonists, is determined by their ability to inhibit the binding of substance P at its receptor sites in CHO-cells which reveal NK1 receptor or IM-9 cells employing radioactive ligands. The substance P antagonist activity of the herein described piperidine compounds is evaluated by using the standard assay procedure described by M. A. Cascieri et al., as reported in *Journal of Biological Chemistry*, Vol. 258, pp. 5158 et seq., 1983. This method essentially involves determining the concentration of the individual compound required to reduce by 50% the amount of radiolabelled substance P ligands at their receptor sites in said isolated cow tissues or IM-9 cells, thereby affording characteristic $IC_{50}$ values for each compound tested. More specifically, inhibition of [$^3$H]SP binding to human IM-9 cells by compounds are determined in assay buffer (50 mM Tris-HCl (pH 7.4), 1 mM $MnCl_2$, 0.02% bovine serum albumin, bacitracin (40 µg/ml), leupeptin (4 µg/ml), chymostatin (2 µg/ml) and phosphoramidon (30 µg/ml)). The reaction is initiated by the addition of cells to assay buffer containing 0.56 nM [$^3$H]SP and various concentrations of compounds (total volume; 0.5 ml) and allowed to incubate for 120 min at 4° C. Incubation is terminated by filtration onto GF/B filters (presoaked in 0.1% polyethylenimine for 2 hours). Nonspecific binding is defined as the radioactivity remaining in the presence of 1 µM SP. The filters are placed into tubes and counted using liquid scintillation counter.

The adverse effect on $Ca^{2+}$ channel binding affinity is determined by study of verapamil binding in a rat heart membrane preparation. More specifically, verapamil binding is performed as previously described by Reynolds et al., (*J. Pharmacol. Exp. Ther.* Vol. 237, pp. 731 et seq., 1986). Briefly, incubations are initiated by the addition of tissue to tubes containing 0.25 nM [$^3$H]desmethoxyverapamil and various concentrations of compounds (total volume; 1 ml). Nonspecific binding is defined as radioligand binding remaining in the presence of 3–10 µM methoxyverapamil.

The activity of the compounds of this invention against CNS disorders is determined in a [$Sar^9$, $Met(O_2)^{11}$] substance P-induced tapping test in gerbils. More specifically, gerbils are lightly anesthetized with ether and the skull surface is exposed. [$Sar^9$, $Met(O_2)^{11}$]substance P or vehicle (5 µl) are administered directly into the lateral ventricles via a 25 gauge needle inserted 3.5 mm below lambda. Following injection, gerbils are placed in 2 l beaker individually and monitored for repetitive hind paw tapping. Some compounds prepared in the following Examples were tested in accordance with these testing methods, and showed good activity in the range of more than 50%-inhibition, at 1.0 mg s.c.

The anti-inflammatory activity of the compounds of this invention, in periphery of a mammalian subject, is demonstrated by a capsaicin-induced plasma extravasation test, using the procedures described by A. Nagahisa et al., as reported in *European Journal of Pharmacology*, Vol. 217, pp. 191–195, 1992. In this testing, anti-inflammatory activity is determined as the percent inhibition of plasma protein extravasation in the ureter of pentbarbital-anesthetized (25 mg/kg i.p.) male Hartley guinea pigs (weighing 300–350 g). Plasma extravasation is induced by intraperitoneal injection of capsaicin (30 µM in 0.1 BSA containing buffer, 10 ml/animal) into the animals and fasted overnight. The compounds of this invention were dissolved in 0.1% methyl cellulose-water and given orally 1 hour before capsaicin challenge. Evans blue dye (30 mg/kg) was administered intravenously 5 minutes before challenge. The animals were killed after capsaicin injection and both right and left ureter were removed. Tissue dye content was qualified after overnight formamide extravasation at 600 nm absorbance. Some compounds, prepared in the working examples as described below, was tested in accordance with the above procedures, and showed good oral activities (i.e., more than 50%-inhibition at 0.1 mg p.o.).

The half life of the compounds of this invention is determined in a human liver microsome preparation. More specifically, the compound (1 µM) was incubated with pooled human liver microsomes (2.0 mg/ml), NADP (1.3 mM), NADH (0.93 mM), glucose-6-phosphate (3.3 mM) $MgCl_2$ (3.3 mM), and glucose-6-phosphate dehydrogenase (8 units/ml) in a total volume of 1.2 ml 100 mM potassium phosphate buffer, pH 7.4. At various time points (0, 5, 10, 30 and 60 min), a 100 µl sample was added to acetonitrile solution (1.0 ml), which included an internal standard. The precipitated protein was spun down in a centrifuge (3,000×g, 5 min). The supernatant w as analyzed by LC-MS. LC-MS unit was consisted of Hewlett Packard HP1090 HPLC system and Sciex API-III. Samples(10 µl) were injected by means of autosampler, onto Hewlett Packard ODS-Hypersil column (2.1×20 mm). A mobile phase was consisted of 80% acetonitrile in 10 mM ammonium acetate. The measurement of API-III was analyzed with multiple reacting monitoring (MRM) detection.

EXAMPLES

The present invention is illustrated by the following examples. However, it should be understood that the invention is not limited to the specific details of these examples. Melting points were taken with a Buchi micro melting point apparatus and uncorrected. Infrared Ray absorption spectra (IR) were measured by a Shimadzu infrared spectrometer (IR-470). $^1$H nuclear magnetic resonance spectra (NMR) was measured in $CDCl_3$ by a JEOL NMR spectrometer (JNM-GX270, 270 MHz for $^1$H) unless otherwise indicated and peak positions are expressed in parts per million (ppm) downfield from tetramethylsilane. The peak shapes are denoted as follows: s, singlet; d, doublet; t, triplet; m, multiplet.

Example 1

Preparation of (2S,3S)-3-(5-(1-Cyanocyclopropyl)-2-methoxybenzyl)amino-2-phenylpiperidine Dihydrochloride (Compound 5)

(i) 4-(1-Cyanocyclopropyl)anisole (Compound 1)

This compound was prepared according to the procedures described in *J. Org. Chem.*, Vol. 37, pp. 2138, 1972.

11

(ii) 5-(1-Cyanocyclopropyl)-2-methoxybenzaldehyde (Compound 2)

To a stirred solution of Compound 1 (2.0 g, 11.6 mmol) in dry $CH_2Cl_2$ (50 ml) was added $TiCl_4$ (5.7 ml, 52.0 mmol) with cooling (−10° C.). After 15 min., to this was added a solution of dichloromethyl methyl ether (2.0 g, 17.3 mmol) in dry $CH_2Cl_2$ (5 ml) dropwise. The reaction mixture was stirred at same temperature for 10 min. and then at room temperature for 1 h. The mixture was poured into ice-water and stirred at room temperature for 15 min. The organic layer was separated and the aqueous layer was extracted with $CH_2Cl_2$. The combined solution was washed with brine, dried ($MgSO_4$) and concentrated in vacuo to give crude product (2.36 g) as a yellow solid. The crude product was recrystallized from hexane-ethyl acetate to give Compound 2 (2.04 g, 88%) as a yellow solid.

$^1$H-NMR ($CDCl_3$) 10.44 (s, 1H), 7.68 (dd, J=8.8, 2.6 Hz, 1H), 7.61 (d, J=2.6 Hz, 1H), 7.01 (d, J=8.8 Hz, 1H), 3.95 (s, 3H), 1.75–1.67 (m, 2H), 1.42–1.35 (m, 2H)

(iii) (2S,3S)-2-Phenylpiperidin-3-amine Dihydrochloride (Compound 3)

This compound was prepared according to the procedures disclosed in EP-558156.

(iv) (2S,3S)-3-(5-(1-Cyanocyclopropyl)-2-methoxybenzyl)amino-2-phenylpiperidine (Compound 4)

To a stirred suspension of Compound 3 (150 mg, 0.60 mmol) and Compound 2 (145 mg, 0.72 mmol) in dry $CH_2Cl_2$ (5 ml) was added $NaBH(OAc)_3$ (358 mg, 1.68 mmol) portionwise at room temperature. The reaction mixture was stirred at room temperature for 6 h. The mixture was basified to pH10–11 with 10% NaOH aq. with ice-cooling. The organic layer was separated and the aqueous layer was extracted with $CH_2Cl_2$. The combined solution was washed with brine, dried ($MgSO_4$) and concentrated in vacuo to give crude product. The crude product (300 mg) was purified by column chromatography on silica gel with $CH_2Cl_2$-MeOH (20:1–10:1) to give Compound 4 (89 mg, 41%) as a yellow viscous oil.

$^1$H-NMR ($CDCl_3$) 7.40–7.20 (m, 5H), 7.15 (dd, J=8.4, 2.6 Hz, 1H), 6.89 (d, J=2.6Hz, 1H), 6.65 (d, J=8.4Hz, 1H), 3.94 (d, J=2.2 Hz, 1H), 3.64 (d, J=14.3 Hz, 1H), 3.48 (s, 3H), 3.40 (d, J=14.3 Hz, 1H), 3.39–3.27 (m, 1H), 2.90–2.75 (m, 2H), 2.20–1.87 (m, 2H), 1.71–1.54 (m, 3H), 1.53–1.40 (m, 1H), 1.30–1.20 (m, 2H).

IR (film) 3330, 2235, 1726, 1609, 1504, 1461, 1455, 1368, 1353, 1327, 1287, 1253, 1180, 1141, 1113, 1085, 1078, 1030, 956, 808, 753, 702.

(v) (2S,3S)-3-(5-(1-Cyanocyclopropyl)-2-methoxybenzyl)amino-2-phenylpiperidine dihydrochloride (Compound 5)

Compound 4 (89 mg, 0.25 mmol) was treated with hydrogen chloride-methanol (5 ml). After the solvent was evaporated in vacuo, the residue (pale yellow solid) was recrystallized from ethanol-diethyl ether to give Compound 5 (91 mg, 85%) as a white solid.

mp: 204°–207° C.: IR (KBr) 3455, 2235, 1560, 1709, 1466, 1455, 1442, 1416, 1335,1256, 1027, 800, 749, 694.

Example 2

Preparation of (2S,3S)-3-(5-(1-(N-Acetyl-N-methylamino)cyclopropyl)-2-methoxybenzyl)amino-2-phenylpiperidine Dihydrochloride (Compound 12)

(i) 4-(1-(N-tert-Butoxycarbonylamino)cyclopropyl) anisole (Compound 6)

A solution of 1-(4-methoxyphenyl)-1-cyclopropanecarboxylic acid (5.00 g, 26.0 mmol), diphe-

12 nylphosphoryl azide (7.87 g, 28.6 mmol) and triethylamine (3.03 g, 29.9 mmol) in t-BuOH (50 ml) was heated at 100° C. for 24 h. After the solvent was evaporated in vacuo, the residue was diluted with $CH_2Cl_2$-$H_2O$. The organic layer was separated and the aqueous layer was extracted with $CH_2Cl_2$. The combined solution was washed with 10% HCl aq., sat. $NaHCO_3$ aq. and brine, dried ($MgSO_4$) and concentrated in vacuo to give crude product (6.86 g) as a pale yellow solid. The crude product was recrystallized from hexane-ethyl acetate to give Compound 6 (4.98 g, 73%) as a white powder solid.

$^1$H-NMR ($CDCl_3$) 7.25–7.15 (m, 2H), 6.87–6.78 (m, 2H), 5.23 and 5.05 (each, br.s, total 1H), 3.78 (s, 3H), 1.42 (s, 9H), 1.25–1.05 (m, 4H)

(ii) 4-(1-Aminocyclopropyl)anisole (Compound 7)

To a stirred solution of Compound 6 (2.00 g, 7.60 mmol) in ethyl acetate (40 ml) was added conc. HCl aq.(10 ml) at room temperature. The reaction mixture was stirred at room temperature for 1 h. The mixture was basified to pH10–11 with 10% NaOH aq. with ice-cooling. The organic layer was separated and the aqueous layer was extracted with AcOEt. The combined solution was washed with brine, dried ($K_2CO_3$) and concentrated in vacuo to give crude Compound 7 (1.26 g, quant.) as a white solid-colorless oil mixture.

$^1$H-NMR (DMSO-d 6) 7.25–7.18 (m, 2H), 6.85–6.79 (m, 2H), 3.71 (s, 3H), 2.21 (br.s, 2H), 0.90–0.77 (m, 4H).

(iii) 4-(1-(N-Acetylamino)cyclopropyl)anisole (Compound 8)

To a stirred suspension of Compound 7 (1.25 g, 7.66 mmol) in $CH_2Cl_2$ (40 ml) was added acetic anhydride (860 mg, 8.42 mmol) and triethylamine (2.32 g, 22.98 mmol) at room temperature. The reaction mixture was stirred at room temperature for 22 h. The mixture was diluted with $H_2O$ (50 ml) and stirred for 10 min. The organic layer was separated and the aqueous layer was extracted with $CH_2Cl_2$. The combined solution was washed with 10% HCl aq., sat. $NaHCO_3$ aq. and brine, dried ($MgSO_4$) and concentrated in vacuo to give crude product (1.58 g, quant.), which was recrystallized from hexane-ethyl acetate to give Compound 8 (1.26 g, 80%) as a white solid.

$^1$H-NMR (DMSO-d 6, 80° C.) 8.22 (br.s, 1H), 7.18–7.04 (m, 2H), 6.90–6.70 (m, 2H), 3.71 (s, 3H), 1.78 (s, 3H), 1.10–0.95 (m, 4H).

(iv) 4-(1-(N-acetyl-N-methylamino)cyclopropyl) anisole (Compound 9)

To a stirred suspension of 60% sodium hydride (234 mg, 5.85 mmol) (washed with pentane) in dry DMF (20 ml) was added Compound 8 (1.00 g, 4.87 mmol) portionwise at room temperature. After 15 min., to this was added iodomethane (1.04 g, 7.31 mmol) at same temperature. The reaction mixture was stirred at room temperature for 2 h. The mixture was diluted with sat. $NH_4Cl$ aq. (20 ml)-$H_2O$ (20 ml) and extracted with toluene-AcOEt (1:2). The combined solution was washed with water and brine, dried($MgSO_4$) and concentrated in vacuo to give crude product (1.05 g) as a yellow solid. The crude product was recrystallized from hexane-ethyl acetate to give Compound 9 (784 mg, 73%) as a white solid.

$^1$H-NMR ($CDCl_3$) 7.25–6.75 (m, 4H), 3.79 and 3.78 (each s, total 3H), 3.04 (s, 3H), 2.08 and 2.06 (each s, total 3H), 1.75–1.15 (m 4H).

(v) 5-(1-(N-Acetyl-N-methylamino)cyclopropyl)-2-methoxybenzaldehyde (Compound 10)

This compound was prepared from Compound 9 in the same manner of Compound 2.

$^1$H-NMR (DMSO-d 6) 10.33 and 10.32 (each s, total 1H), 7.50–7.10 (m, 3H), 3.91 and 3.89 (each s, total 3H), 2.99 and 2.90 (each s, total 3H), 2.00 and 1.92 (each s, total 3H), 1.70–1.00 (m, 4H)

(vi) (2S,3S)-3-(5-(1-(N-Acetyl-N-methylamino)cyclopropyl)-2-methoxybenzyl)amino-2-phenylpiperidine (Compound 11)

This compound was prepared from Compound 3 and Compound 10 in the same manner of Compound 4

$^1$H-NMR (CDCl$_3$) 7.40–7.20 (m, 5H), 6.80 (dd, J=8.4, 2.6 Hz, 1H), 6.64 (d, J=8.4 Hz, 1H), 6.57 (d, J=2.6 Hz, 1H), 3.99 (d, J=1.8 Hz, 1H), 3.66 (d, J=13.9 Hz, 1H), 3.47 (s, 3H), 3.38 (d, J=13.9 Hz, 1H), 3.50–3.30 (m, 1H), 3.00 (s, 3H), 3.05–2.75 (m, 2H), 2.25–1.90 (m, 2H), 2.05 (s, 3H), 1.75–1.10 (m, 6H).

IR(film) 3430, 3305, 1652, 1642, 1636, 1505, 1464, 1455, 1387, 1250, 1140, 1032, 911, 731.

(vii) (2S,3S)-3-(5-(1-(N-Acetyl-N-methylamino)cyclopropyl)-2-methoxybenzyl)amino-2-phenylpiperidine Dihydrochloride (Compound 12)

This compound was prepared from Compound 11 in the same manner of Compound 5.

mp: 226°–228° C. (decomp.). IR(KBr)3460, 1658, 1551, 1509, 1455, 1444, 1414, 1375, 1334, 1252, 1170, 1142, 1029, 748, 693.

Example 3

Preparation of (2S,3S)-3-(5-(1-Cyanoethyl)-2-methoxybenzyl)amino-2-phenyl-1-piperidine Dihydrochloride (Compound 20)

(i) 2-(4-methoxyphenyl)propionitrile (Compound 13)

To a mixture of 4-methoxyphenylacetonitrile (17 g, 0.11 mol) and MeLi (1M; 100 ml, 0.11 mol) in THF (200 ml) was added MeI (32 g, 0.22 mol) at −78° C. After the mixture was stirred for 3 hours, the mixture was poured into H$_2$O (100 ml), and extracted with AcOEt. The combined extracts were dried (Na$_2$SO$_4$), and concentrated to give a yellow oil (20 g), which was purified by a column chromatography on silica gel to give Compound 13 as a colorless oil (11 g, 62%).

$^1$H-NMR (CDCl$_3$) 7.27 (d, J=9 Hz, 2H), 6.91 (d, J=9 Hz, 2H), 3.85 (q, J=7 Hz, 1H), 3.81 (s, 3H), 1.62 (d, J=7 Hz, 3H)

(ii) 5-(1-Cyanoethyl)-2-methoxybenzaldehyde (Compound 14)

This compound was prepared from Compound 13 in the same manner of Compound 2.

$^1$H-NMR (CDCl$_3$) 10.46 (s, 1H), 7.81–6.99 (m, 3H), 3.96 (s, 3H), 3.90 (q, J=7 Hz, 1H), 1.64 (d, J=7 Hz, 3H)

(iii) (2S,3S)-3-(2-Methoxybenzyl)amino-2-phenylpiperidine (Compound 15)

This compound was prepared according to the procedures described in WO-93-01170.

(iv) (2S,3S)-1-tert-Butoxycarbonyl-3-(2-methoxybenzyl)amino-2-phenylpiperidine (Compound 16)

To a stirred and ice-cooled mixture of Compound 15 (10 g, 27 mmol), 3M NaOH aq. (36 ml, 110 mmol) and tert-BuOH (15 ml) was added (tert-BuOCO)$_2$O (7.4 g, 34 mmol) in one portion. After stirring at room temperature overnight, the mixture was extracted with AcOEt. The combined AcOEt extracts were washed with H$_2$O, and sat. NaCl aq, dried (Na$_2$SO$_4$), and concentrated in vacuo to give Compound 16 (11 g, quant.) as a pale yellow oil.

$^1$H-NMR (CDCl$_3$) 7.58 (br.d, J=7.3 Hz, 2H), 7.36–7.16 (m, 5H), 6.89 (ddd, J=7.5, 7.5, 1.1 Hz, 1H), 6.81 (dd, J=8.4, 0.8 Hz, 1H), 5.47 (br.s, 1H), 3.96 (dm, J=13.4 Hz, 1H), 3.87 (d, J=13.6 Hz, 1H), 3.79 (d, J=13.6 Hz, 1H), 3.70 (s, 3H), 3.10–2.99 (m, 1H), 2.94 (dd, J=12.5, 3.4 Hz, 1H), 1.87–1.74 (m, 2H), 1.74–1.40 (m, 3H), 1.41 (s, 9H)

This was employed in the next step without further purification.

(v) (2S,3S)-3-Amino-1-tert-butoxycarbonyl-2-phenylpiperidine (Compound 17)

A mixture of Compound 16 (11 g), 20% Pd(OH)$_2$/C (3.1 g), and MeOH (90 ml) was stirred under an atmosphere of H$_2$ at room temperature overnight. After an additional amount of 20% Pd(OH)$_2$/C (0.55 g) was added, the stirring was continued under an atmosphere of H$_2$ at room temperature for three days. The catalyst was filtered off by the aid of celite, and washed with MeOH thoroughly. The combined MeOH filtrate and washings were concentrated in vacuo to give crude Compound 17 (8.6 g, quant.).

This was dissolved in EtOH (20 ml), and then a warmed solution of fumaric acid (1.6 g, 13.5 mmol) in EtOH (20 ml)was added in one portion to this solution at room temperature. The crystals precipitated were collected by filtration, washed with ice-chilled EtOH, and dried in vacuo at 50° C. to give (2S,3S)-3-amino-1-(tert-butoxycarbonyl)-2-phenylpiperidine semifumarate (6.1 g, 68%) as white short needles.

After a suspension of semifumarate (1.2 g, 3.7 mmol) in H$_2$O was ice-cooled, 20% NaOH aq. was added until the mixture became basic. The mixture was then extracted with AcOEt. The combined AcOEt extracts were washed with sat. NaCl aq., dried (Na$_2$SO$_4$), and concentrated in vacuo to give pure Compound 17 (0.95 g, 93%).

$^1$H-NMR (CDCl$_3$) 7.47–7.39 (m, 2H), 7.37–7.23 (m, 5H), 5.19 (br.d, J=6.2 Hz, 1H), 4.00 (dm, J=13.0 Hz, 1H), 3.25–3.05 (m, 2H), 1.94–1.83 (m, 1H), 1.83–1.56 (m, 4H), 1.36 (s, 9H), 1.32 (br.s, 2H)

(vi) (2S,3S)-1-tert-Butoxycarbonyl-3-(5-(1-cyanoethyl)-2-methoxybenzyl)amino-2-phenylpiperidine (Compound 18)

To a stirred and ice-cooled solution of Compound 17 (160 mg, 0.60 mmol) and Compound 14 (120 mg, 0.60 mmol) in dry CH$_2$Cl$_2$ (5 ml) was added NaBH(OAc)$_3$ (430 mg, 2.0 mmol) in one portion. The mixture was stirred at room temperature for 20 hours. The mixture was poured into NaHCO$_3$ aq., and extracted with CH$_2$Cl$_2$. The combined extracts were dried (Na$_2$SO$_4$), and concentrated in vacuo to give Compound 18 as a yellow oil (280 mg).

$^1$H-NMR (CDCl$_3$) 7.61–6.73 (m, 8H), 5.30 (br, 1H), 4.00–2.90 (m, 6H), 3.70 (s, 3H), 1.90–1.40 (m, 4H), 1.59 (d, J=7 Hz, 3H), 1.40 (s, 9H)

This was employed in the next step without further purification.

(vii) (2S,3S)-3-(5-(1-cyanoethyl)-2-methoxybenzyl)amino-2-phenylpiperidine (Compound 19)

To a solution of Compound 18 (280 mg) in AcOEt (6 ml) was added conc. HCl (1 ml). The mixture was stirred at room temperature for 45 minutes. The mixture was extracted with $CH_2Cl_2$. The combined extracts were dried ($Na_2SO_4$), and concentrated in vacuo to give Compound 19 as a yellow oil.

$^1$H-NMR ($CDCl_3$)

This was employed in the next step without further purification.

(viii) (2S,3S)-3-(5-(1-cyanoethyl)-2-methoxybenzyl) amino-2-phenylpiperidine Dihydrochloride (Compound 20)

To a solution of Compound 19 in $CH_2Cl_2$ (10 ml) was added an excess amount of 10% HCl-MeOH (6 ml). After the solvent was evaporated in vacuo, the residual solid was recrystallized from IPA to give Compound 20 (90 mg, 36%; three steps) as a colorless crystal.

mp 261°–265° C.

Example 4

Preparation of (2S,3S)-3-(2-methoxy-5-(1,1-dimethyl-2-propynyl)benzyl)amino-2-phenylpiperidine Dihydrochloride (Compound 25)

(i) 4-(1,1-dimethyl-2-propynyl)anisole (Compound 21)

This compound was prepared according to the procedures described in *Tetrahedron Lett.*, p. 4163, 1977.

(ii) 2-methoxy-5-(1,1-dimethyl-2-propynyl) benzaldehyde (Compound 22)

This compound was prepared from Compound 21 in the same manner of Compound 2.

$^1$H-NMR ($CDCl_3$) 10.47 (s, 1H), 8.00–6.91 (m, 3H), 3.93 (s, 3H), 2.36 (s, 1H), 1.59 (s, 6H)

(iii) (2S,3S)-1-tert-Butoxycarbonyl-3-(2-methoxy-5-(1,1-dimethyl-2-propynyl)benzyl)amino-2-phenylpiperidine (Compound 23)

This compound was prepared from Compound 22 and Compound 17 in the same manner of Compound 18.

$^1$H-NMR ($CDCl_3$) 7.63–6.71 (m, 8H), 5.46 (br, 1H), 4.02–2.96 (m, 5H), 3.70 (s, 3H), 1.93–1.40 (m, 4H), 1.56 (s, 3H), 1.56 (s, 3H), 1.40 (s, 9H)

This was employed in the next step without further purification.

(iv) (2S,3S)-3-(2-methoxy-5-(1,1-dimethyl-2-propynyl)benzyl)amino-2-phenylpiperidine (Compound 24)

This compound was prepared from Compound 23 in the same manner of Compound 19.

$^1$H-NMR ($CDCl_3$) 7.38–6.58 (m, 8H), 3.89–2.73 (m, 5H), 3.46 (s, 3H), 2.31 (s, 1H), 2.20–1.40 (m, 4H), 1.53 (s, 6H)

This was employed in the next step without further purification.

(v) (2S,3S)-3-(2-methoxy-5-(1,1-dimethyl-2-propynyl)benzyl)amino-2-phenylpiperidine Dihydrochloride (Compound 25)

This compound was prepared from Compound 24 in the same manner of Compound 20.

mp 260°–263° C.

Example 5

Preparation of (2S,3S)-3-(5-(1-cyano-1-methylethyl)-2-methoxybenzyl)amino-2-phenylpiperidine Dihydrochloride (Compound 28)

(i) 2-(4-methoxyphenyl)-2-methylpropionitrile (Compound 26)

To a mixture of 4-methoxyphenylacetonitrile (17 g, 0.11 mol) and MeLi (1M; 200 ml, 0.22 mol) in THF (200 ml) was added MeI (32 g, 0.22 mol) at −78° C. After the mixture was stirred for 4 hours, the mixture was poured into $H_2O$ (100 ml), and extracted with AcOEt. The combined extracts were dried ($Na_2SO_4$), and concentrated to give a yellow oil (21 g), which was purified by a column chromatography on silica gel to give Compound 26 as a colorless oil (16 g, 83%).

$^1$H-NMR ($CDCl_3$) 7.39 (d, J=9 Hz, 2H), 6.91 (d, J=9 Hz, 2H), 3.81 (s, 3H), 1.70 (s, 6H)

(ii) 5-(1-Cyano-1-methylethyl)-2-methoxybenzaldehyde (Compound 27)

This compound was prepared from Compound 26 in the same manner of Compound 2.

$^1$H-NMR ($CDCl_3$) 10.47 (s, 1H), 7.89–7.00 (m, 3H), 3.96 (s, 3H), 1.73 (s, 6H)

(iii) (2S,3S)-3-(5-(1-cyano-1-methylethyl)-2-methoxybenzyl)amino-2-phenylpiperidine Dihydrochloride (Compound 28)

This compound was prepared from Compound 27 and Compound 3 in the same manner of Compound 5.

$^1$H-NMR(free base, $CDCl_3$) 7.38–6.62 (m, 8H), 3.95–3.22 (m, 4H), 3.49 (s, 3H), 2.89–1.38 (m, 6H), 1.64 (s, 6H)

mp 281°–286° C.

Example 6

Preparation of (2S,3S)-3-(5-(1-methoxycarbonylethyl)-2-methoxybenzyl)amino-2-phenylpiperidine Dihydrochloride (Compound 34)

(i) 4-(1-methoxycarbonylethyl)anisole (Compound 32)

This compound was prepared according to the procedures described in *Tetrahedron Lett.*, p. 4163, 1977.

(ii) 2-methoxy-5-(1-methoxycarbonylethyl) benzaldehyde (Compound 33)

This compound was prepared from Compound 32 in the same manner of Compound 2.

$^1$H-NMR ($CDCl_3$) 10.45 (s, 1H), 7.80–6.95 (m, 3H), 3.92 (s, 3H), 3.73 (q, J=7 Hz, 1H), 3.66 (s, 3H), 1.50 (d, J=7 Hz, 3H)

(iii) (2S,3S)-3-(5-(1-methoxycarbonylethyl)benzyl) amino-2-phenylpiperidine Dihydrochloride (Compound 34)

This compound was prepared from Compound 33 and Compound 3 in the same manner of Compound 5.

$^1$H-NMR ($CDCl_3$, free base) 7.38–6.58 (m, 8H), 3.96–2.73 (m, 7H), 3.65 (s, 3H), 3.44 (s, 3H), 2.22–1.53 (m, 4H), 1.42 (d, J=6 Hz, 3H)

mp 250°–253° C.

Example 7

Preparation of (2S,3S)-3-(5-(1,1-dicyanoethyl)-2-methoxybenzyl)amino-2-phenylpiperidine Dihydrochloride (Compound 39

(i) 4-(dicyanomethyl)anisole (Compound 35)

To a mixture of 4-iodoanisole (2.3 g, 10 mmol), malononitrile (750 mg, 11 mmol) and KOBu-t (2.5 g, 22 mmol) in THF (40 ml) was added PdCl$_2$(PPh$_3$)$_2$ (300 mg, 0.4 mmol) at room temperature. After the mixture was refluxed for 25 hours, the mixture was poured into H$_2$O (10 ml), and extracted with ether. The combined extracts were dried (Na$_2$SO$_4$), and concentrated to give a yellow oil, which was purified by a column chromatography on silica gel to give Compound 35 as a colorless solid (1.1 g, 64%).

$^1$H-NMR (CDCl$_3$) 7.41 (d, J=9 Hz, 2H), 6.99 (d, J=9 Hz, 2H), 5.01 (s, 1H), 3.85 (s, 3H)

(ii) 4-(1,1-dicyanoethyl)anisole (Compound 36)

To a mixture of Compound 35 (1.0 g, 6.0 mmol) and NaH (280 mg, 7.0 mmol) in DMF (12 ml) was added MeI (1.0 g, 7.0 mmol) at room temperature. After the mixture was stirred for 22 hours, the mixture was poured into H$_2$O (30 ml), and extracted with CH$_2$Cl$_2$. The combined extracts were dried (Na$_2$SO$_4$), and concentrated to give a yellow oil (3 g), which was purified by a column chromatography on silica gel to give Compound 35 as a colorless solid (900 mg, 81%).

$^1$H-NMR (CDCl$_3$) 7.49 (d, J=9 Hz, 2H), 6.99 (d, J=9 Hz, 2H), 3.84 (s, 3H), 2.09 (s, 3H)

(iii) 5-(1,1-dicyanoethyl)-2-methoxybenzaldehyde (Compound 37)

This compound was prepared from Compound 36 in the same manner of Compound 2.

$^1$H-NMR (CDCl$_3$) 10.47 (s, 1H), 8.08–7.10 (m, 3H), 4.00 (s, 3H), 2.13 (s, 3H)

(iv) (2S,3S)-3-(5-(1,1-dicyanoethyl)-2-methoxybenzyl)amino-2-phenylpiperidine Dihydrochloride (Compound 38)

This compound was prepared from Compound 37 and Compound 3 in the same manner of Compound 5.

$^1$H-NMR (CDCl$_3$, free base) 7.40–6.65 (m, 8H), 3.95–2.75 (m, 6H), 3.55 (s, 3H), 2.20–1.40 (m, 4H), 2.02 (s, 3H) mp 281°–285° C.

Example 8

Preparation of (2S,3S)-3-(5-(1-Cyano-1-methylethyl)-2-isopropoxybenzyl)amino-2-phenylpiperidine Dihydrochloride (Compound 44)

(i) 2-(4-Hydroxyphenyl)-2-methylpropionitrile (Compound 39)

To a stirred solution of Compound 26 (3.0 g, 17 mmol) in CH$_2$Cl$_2$ (20 ml) was added BBr$_3$ (1.0M in CH$_2$Cl$_2$, 38 ml, 38 mmol) under nitrogen at room temperature, and stirred for 3 h. The mixture was poured into ice-water. The aqueous layer was extracted with CH$_2$Cl$_2$, and the organic layers were combined, washed with brine, dried (MgSO$_4$), filtered, and concentrated. This solid was recrystallized from AcOEt-hexane to give Compound 39 (1.9 g, 70%) as a white solid.

$^1$H-NMR (CDCl$_3$) 7.33 (d, 2H, J=8.4 Hz), 6.84 (d, 2H, J=8.4 Hz), 5.10 (1H), 1.70 (s, 6H)

(ii) 2-(4-Isopropoxyphenyl)-2-methylpropionitrile (Compound 40)

To a stirred solution of Compound 39 (500 mg, 3.10 mmol) and 2-Iodopropane (0.930 ml, 9.30 mmol) in acetone (8 ml) was added Cs$_2$CO$_3$ (4.55 g, 14.0 mmol), and refluxed for 2 h. The mixture was filtered over celite and washed with acetone. The filtrate was concentrated to give crude Compound 40. This was diluted with AcOEt, washed with water and brine, dried (MgSO$_4$), and concentrated. This was purified by a column chromatography on silica gel to give Compound 40 (610 mg, 97%) as a colorless oil.

$^1$H-NMR (CDCl$_3$) 7.36 (d, 2H, J=9.0 Hz), 6.88 (d, 2H, J=9.0 Hz), 4.55 (hep, 1H, J=5.9 Hz), 1.70 (s, 6H), 1.34 (d, 6H, J=5.9 Hz)

(iii) 5-(1-Cyano-1-methylethyl)-2-isopropoxybenzaldehyde (Compound 41)

This compound was prepared from Compound 40 in the same manner of Compound 2.

$^1$H-NMR (CDCl$_3$) 10.47 (s, 1H), 7.84 (d, 1H, J=2.9 Hz), 7.71 (dd, 1H, J=8.8, 2.9 Hz), 7.02 (d, 1H, J=8.8 Hz), 4.71 (hep, 1H, J=5.9 Hz), 1.72 (s, 6H), 1.42 (d, 6H, J=5.9 Hz)

(iv) (2S,3S)-1-tert-Butoxycarbonyl-3-(5-(1-cyano-1-methylethyl)-2-isopropoxybenzyl)amino-2-phenylpiperidine (Compound 42)

This compound was prepared from Compound 41 and Compound 17 in the same manner of Compound 18.

$^1$H-NMR (CDCl$_3$) 7.63–7.56 (m, 2H), 7.38–7.22 (m, 5H), 6.82–6.78 (m, 1H), 5.52–5.41 (m, 1H), 4.51 (hep, 1H, J=6.1 Hz), 4.03–3.92 (m, 1H), 3.82 (d, 1H, J=13.6 Hz), 3.80 (d, 1H, J=13.6 Hz), 3.12–2.95 (m, 2H), 1.98–1.60 (m, 4H), 1.68 (s, 6H), 1.40 (s, 9H), 1.26 (d, 3H, J=6.1 Hz), 1.23 (d, 3H, J=6.1 Hz)

(v) (2S,3S)-3-(5-(1-Cyano-1-methylethyl)-2-isopropoxybenzyl)amino-2-phenylpiperidine (Compound 43)

This compound was prepared from Compound 42 in the same manner of Compound 19.

$^1$H-NMR (CDCl$_3$) 7.32–7.18 (m, 6H), 7.08 (d, 1H, J=2.6 Hz), 6.69 (d, 1H, J=8.8 Hz), 4.36 (hep, 1H, J=6.1 Hz), 3.89 (d, 1H, J=2.2 Hz), 3.57 (d, 1H, J=13.7 Hz), 3.39 (d, 1H, J=13.7 Hz), 3.34–3.25 (m, 1H), 2.93–2.88 (m, 1H), 2.81 (dt, 1H, J=12.5, 3.3 Hz), 2.22–2.12 (m, 1H), 1.96–1.85 (m, 1H), 1.80–1.60 (m, 1H), 1.64 (s, 3H), 1.63 (s, 3H), 1.49–1.38 (m, 1H), 1.13 (d, 3H, J=6.1 Hz), 1.09 (d, 3H, J=6.1 Hz)

(vi) (2S,3S)-3-(5-(1-Cyano-1-methylethyl)-2-isopropoxybenzyl)amino-2-phenylpiperidine Dihydrochloride (Compound 44)

This compound was prepared from Compound 43 in the same manner of Compound 20.

mp 273°–274° C. IR (KBr) 3470, 2920, 2660, 2465, 1554, 1502, 1451, 1259, 1136, 955

Example 9

Preparation of (2S,3S)-3-(5-(2-Cyano-1,1-dimethylethyl)-2-methoxybenzyl)amino-2-phenylpiperidine Dihydrochloride (Compound 48)

(i) 2-(4-Methoxyphenyl)-2-methylpropionaldehyde (Compound 45)

To a solution of Compound 26 (5.3 g, 30 mmol) in benzene (20 ml) was added a solution of iBu$_2$AlH in toluene (40 ml, 42 mmol) at room temperature. The reaction mixture was stirred at room temperature for 2 h. The mixture was quenched with HCl aq. (200 ml), and extracted with AcOEt (200 ml×2). The combined extracts were dried (Na$_2$SO$_4$)

and concentrated in vacuo to give crude which was purified by a column chromatography to give Compound 45 (2.7 g, 15 mmol, 50%) as a colorless oil.

$^1$H-NMR (CDCl$_3$) 9.45 (s, 1H), 7.19 (d, J=9 Hz, 2H), 6.91 (d, J=9 Hz, 2H), 3.81 (s, 3H), 1.44 (s, 6H)

(ii) 3-(4-Methoxyphenyl)-3-methylbutyronitrile (Compound 46)

To a mixture of KOBu-t (450 mg, 4.2 mmol) and TosCH$_2$NCO (410 mg, 2.1 mmol) in DME (8 ml) was added a solution of Compound 45 (350 mg, 2.0 mmol) in DME (2 ml) with cooling (−40° C.). The mixture was stirred at same temperature for 10 min. and then at room temperature for 1 h and to this was added MeOH (6 ml) dropwise. The mixture was stirred at same temperature for 1 hr. and then at room temperature for 15 h. The mixture was concentrated to give a solid, which was dissolved in water (10 ml). The aqueous layer was extracted with CH$_2$Cl$_2$. The combined extracts were dried (Na$_2$SO$_4$) and concentrated in vacuo to give crude product (480 mg) as a yellow oil. The crude product was purified by a column chromatography to give Compound 46 (230 mg, 1.2 mmol., 60%) as a colorless solid.

$^1$H-NMR (CDCl$_3$) 7.30 (d, J=9 Hz, 2H), 6.89 (d, J=9 Hz, 2H), 3.80 (s, 3H), 2.58 (s, 2H), 1.49 (s, 6H)

(iii) 5-(2-Cyano-1,1-dimethylethyl)-2-methoxybenzaldehyde (Compound 47)

This compound was prepared from Compound 46 in the same manner of Compound 2.

$^1$H-NMR (CDCl$_3$) 10.47 (s, 1H), 7.85–6.96 (m, 3H), 3.94 (s, 3H), 2.58 (s, 2H), 1.51 (s, 6 H)

(iv) (2S,3S)-3-(5-(2-Cyano-1,1-dimethylethyl)-2-methoxybenzyl)amino-2-phenylpiperidine Dihydrochloride (Compound 48)

This compound was prepared from Compound 47 and Compound 3 in the same manner of Compound 5.

$^1$H-NMR(free base, CDCl$_3$) 7.38–6.60 (m, 8H), 3.92–3.20 (m, 4H), 3.49 (s, 3H), 2.88–1.38 (m, 6H), 2.49 (s, 2H), 1.72 (s, 6H)

mp 265°–270° C.

Example 10

Preparation of (2S,3S)-3-(5-(1-Cyanocyclohexyl)-2-methoxybenzyl)amino-2-phenylpiperidine Dihydrochloride (Compound 50)

(i) 5-(1-Cyanocyclohexyl)-2-methoxybenzaldehyde (Compound 49)

This compound was prepared from 4-(1-Cyanocyclohexyl)anisole in the same manner of Compound 2.

$^1$H-NMR (CDCl$_3$) 10.46 (s, 1H), 7.88–7.00 (m, 3H), 3.95 (s, 3H), 2.21–1.20 (s, 10H)

(ii) (2S,3S)-3-(5-(1-Cyanocyclohexyl)-2-methoxybenzyl)amino-2-phenylpiperidine Dihydrochloride (Compound 50)

This compound was prepared from Compound 47 and Compound 3 in the same manner of Compound 5.

$^1$H-NMR(free base, CDCl$_3$) 7.40–6.62 (m, 8H), 4.00–2.78 (m, 6H), 3.48 (s, 3H), 2.22–1.18 (m, 14H)

mp 272°–280° C.

Example 11

Preparation of (2S,3S)-3-(5-(1-Cyanocyclopentyl)-2-methoxybenzyl)amino-2-phenylpiperidine Dihydrochloride (Compound 52)

(i) 5-(1-Cyanocyclopentyl)-2-methoxybenzaldehyde (Compound 51)

This compound was prepared from 4-(1-Cyanocyclohexyl)anisole in the same manner of Compound 2.

$^1$H-NMR (CDCl$_3$) 10.46 (s, 1H), 7.88–7.00 (m, 3H), 3.96 (s, 3H), 2.56–1.86 (s, 10H)

(ii) (2S,3S)-3-(5-(1-Cyanocyclopentyl)-2-methoxybenzyl)amino-2-phenylpiperidine Dihydrochloride (Compound 52)

This compound was prepared from Compound 51 and Compound 3 in the same manner of Compound 5.

$^1$H-NMR(free base, CDCl$_3$) 7.42–6.64 (m, 8H), 4.09–2.83 (m, 6H), 3.48 (s, 3H), 2.46–1.52 (m, 12H)

mp265°–272° C.

Example 12

Preparation of (2S,3S)-3-|5-(1,1-dimethyl-2-butynyl)-2-methoxybenzyl|amino-2-phenylpiperidine Dihydrochloride (Compound 57)

(i) 4-(1,1-Dimethyl-3,3-dibromo-2-propenyl)anisole (Compound 53)

To a stirred solution of Compound 45 (3.0 g, 17 mmol) and CBr$_4$ (11 g, 34 mmol) in CH$_2$Cl$_2$ (100 ml) was added PPh$_3$ (18 g, 67 mmol) at r.t., and stirred for 1.5 h. The mixture was quenched by the addition of H$_2$O, and extracted with CH$_2$Cl$_2$. The combined organic layers were washed with brine, dried over MgSO$_4$, filtered, and concentrated. This was purified by SiO$_2$ chromatography to give Compound 53 (2.5 g, 45%) as a colorless oil.

$^1$H-NMR (270 MHz) (CDCl$_3$) 7.23 (d, 2H, J=8.8 Hz), 6.89 (s, 1H), 6.84 (d, 2H, J=8.8 Hz), 3.80 (s, 3H), 1.50 (6H, s) ppm.

(ii) 4-(1,1-Dimethyl-2-butynyl)anisole (Compound 54)

To a stirred solution of Compound 53 (335 mg, 1.00 mmol) in THF (10 ml) was added n-BuLi (1.69M in hexane, 1.19 ml, 2.01 mmol) at −78° C. under N$_2$, then warmed up to 0° C., and stirred for 1.5 h. MeI (213 mg, 1.50 mmol) was added, and stirred for 1.5 h at 0° C. The mixture was quenched by the addition of NH$_4$Cl aq., and extracted with CH$_2$Cl$_2$. The combined organic layers were dried over MgSO$_4$, filtered, and concentrated. This was purified by SiO$_2$ chromatography to give Compound 54 (162 mg, 86%) as a colorless oil.

$^1$H-NMR (270 MHz) (CDCl$_3$) 7.46 (d, 2H, J=9.2 Hz), 6.84 (d, 2H, J=9.2 Hz), 3.76 (s, 3H), 1.85 (s, 3H), 1.52 (6H, s) ppm.

(iii) 5-(1,1-Dimethyl-2-butynyl)-2-methoxybenzaldehyde (Compound 55)

This compound was prepared from Compound 54 in the same manner of Compound 2.

$^1$H-NMR (270 MHz) (CDCl$_3$) 10.46 (s, 1H), 7.95 (d, 1H, J=2.6 Hz), 7.80 (dd, 1H, J=8.8, 2.6 Hz), 6.95 (d, 1H, J=8.8 Hz), 3.92 (s, 3H), 1.87 (s, 3H), 1.54 (6H, s) ppm.

(iv) (2S,3S)-1-tert-Butoxycarbonyl-3-[5-(1,1-dimethyl-2-butynyl)-2-methoxybenzyl]amino-2-phenylpiperidine (Compound 56)

This compound was prepared from Compound 55 and Compound 17 in the same manner of Compound 18.

$^1$H-NMR (270 MHz) (CDCl$_3$) 7.64–7.55 (m, 2H), 7.43–7.20 (m, 5H), 6.75 (d, 1H, J=8.8 Hz), 5.52–5.42 (m, 1H), 4.02–3.92 (m, 1H), 3.83 (s, 2H), 3.69 (s, 3H), 3.13–2.94 (m, 2H), 1.95–1.50 (m, 4H), 1.85 (s, 3H), 1.51 (s, 3H), 1.50 (s, 3H), 1.40 (9H, s) ppm.

(v) (2S,3S)-3-[5-(1,1-Dimethyl-2-butynyl)-2-methoxybenzyl]amino-2-phenylpiperidine Dihydrochloride (Compound 57)

To a solution of Compound 56 (73 mg, 0.15 mmol) in AcOEt (6 ml) was added an excess amount of 10% HCl-MeOH (3 ml), and stirred for 18 h. After the solvent was evaporated in vacuo, the residual solid was recrystallized from MeOH-ether to give Compound 57 (48 mg, 78%) as a white solid.

mp 220°–222° C. IR (KBr) 3430, 2935, 2665, 1560, 1506, 1455, 1413, 1259, 1029 cm$^{-1}$. $^1$H-NMR (270 MHz) (free base; CDCl$_3$) 7.40–7.15 (m, 7H), 6.63 (d, 1H, J=8.4 Hz), 3.92 (d, 1H, J=2.2 Hz), 3.72 (d, 1H, J=13.9 Hz), 3.50–3.42 (m, 1H), 3.43 (s, 3H), 3.40–3.30 (m, 1H), 2.90–2.75 (m, 2H), 2.25–1.40 (m, 4H), 1.85 (s, 3H), 1.49 (s, 6H) ppm.

Example 13

Preparation of (2S,3S)-3-[5-(1,1-dimethyl-3-methoxycarbonyl-2-propynyl)-2-methoxybenzyl]amino-2-phenylpiperidine Dihydrochloride (Compound 61)

(i) 4-(1,1-Dimethyl-3-methoxycarbonyl-2-propynyl) anisole (Compound 58)

This compound was prepared from Compound 53 and ClCO$_2$Me in the same manner of Compound 54.

$^1$H-NMR (270 MHz) (CDCl$_3$) 7.41 (d, 2H, J=8.8 Hz), 6.87 (d, 2H, J=8.8 Hz), 3.80 (s, 3H), 3.78 (s, 3H), 1.63 (6H, s) ppm.

(ii) 5-(1,1-Dimethyl-3-methoxycarbonyl-2-propynyl)-2-methoxybenzaldehyde (Compound 59)

This compound was prepared from Compound 58 in the same manner of Compound 2.

$^1$H-NMR (270 MHz) (CDCl$_3$) 10.46 (s, 1H), 7.88 (d, 1H, J=2.6 Hz), 7.77 (dd, 1H, J 8.8, 2.6 Hz), 6.99 (d, 1H, J=8.8 Hz), 3.94 (s, 3H), 3.78 (s, 3H), 1.64 (s, 6H) ppm.

(iii) (2S,3S)-1-tert-Butoxycarbonyl-3-[5-(1,1-dimethyl-3-methoxycarbonyl-2-propynyl)-2-methoxybenzyl]amino-2-phenylpiperidine (Compound 60)

This compound was prepared from Compound 59 and Compound 17 in the same manner of Compound 18.

$^1$H-NMR (270 MHz) (CDCl$_3$) 7.63–7.57 (m, 2H), 7.38–7.20 (m, 5H), 6.77 (d, 1H, J=8.4 Hz), 5.50–5.42 (m, 1H), 4.00–3.88 (m, 1H), 3.82 (s, 2H), 3.77 (s, 3H), 3.69 (s, 3H), 3.12–2.94 (m, 2H), 1.95–1.50 (m, 4H), 1.60 (s, 3H), 1.59 (s, 3H), 1.40 (9H, s) ppm.

(iv) (2S,3S)-3-[5-(1,1-Dimethyl-3-methoxycarbonyl-2-propynyl)-2-methoxybenzyl]amino-2-phenylpiperidine Dihydrochloride (Compound 61)

This compound was prepared from Compound 60 in the same manner of Compound 57.

mp 216°–218° C. IR (KBr) 3430, 2930, 2735, 2230, 1712, 1508, 1453, 1258, 1030, 750, 692 cm$^{-1}$. $^1$H-NMR (270 MHz) (free base; CDCl$_3$) 7.38–7.18 (m, 7H), 6.64 (d, 1H, J=8.8 Hz), 3.90 (d, 1H, J 2.2 Hz), 3.78 (s, 3H), 3.65 (d, 1H, J=13.9 Hz), 3.46 (s, 3H), 3.40 (d, 1H, J=13.9 Hz), 3.32–3.23 (m, 1H), 2.88–2.74 (m, 2H), 2.20–2.08 (m, 1H), 2.05–1.75 (m, 1H), 1.70–1.55 (m, 1H), 1.57 (s, 6H) 1.47–1.35 (m, 1H) ppm.

Example 14

Preparation of (2S,3S)-3-[5-(3-cyano-1,1-dimethyl-2-propynyl)-2-methoxybenzyl]amino-2-phenylpiperidine Dihydrochloride (Compound 66)

(i) Phenylcyanate (Compound 62)

This compound was prepared according to the procedures described in Synthesis Communication, pp. 150–151, February, 1980.

(ii) 4-(3-Cyano-1,1-dimethyl-2-propynyl)anisole (Compound 63)

This compound was prepared from Compound 53 and Compound 62 in the same manner of Compound 54.

$^1$H-NMR (270 MHz) (CDCl$_3$) 7.34 (d, 2H, J=8.8 Hz), 6.90 (d, 2H, J=8.8 Hz), 3.81 (s, 3H), 1.64 (6H, s) ppm.

(iii) 5-(3-Cyano-1,1-dimethyl-2-propynyl)-2-methoxybenzaldehyde (Compound 64)

This compound was prepared from Compound 63 in the same manner of Compound 2.

$^1$H-NMR (270 MHz) (CDCl$_3$) 10.46 (s, 1H), 7.85 (d, 1H, J=2.6 Hz), 7.67 (dd, 1H, J=8.8, 2.6 Hz), 7.03 (d, 1H, J=8.8 Hz), 3.95 (s, 3H), 1.67 (s, 6H) ppm.

(iv) (2S,3S)-1-tert-Butoxycarbonyl-3-[5-(3-cyano-1,1-dimethyl-2-propynyl)-2-methoxybenzyl]amino-2-phenylpiperidine (Compound 65)

This compound was prepared from Compound 64 and Compound 17 in the same manner of Compound 18.

$^1$H-NMR (270 MHz) (CDCl$_3$) 7.64–7.56 (m, 2H), 7.38–7.22 (m, 5H), 6.78 (d, 1H, J=8.4 Hz), 5.54–5.42 (m, 1H), 4.02–3.90 (m, 1H), 3.83 (s, 2H), 3.70 (s, 3H), 3.12–2.93 (m, 2H), 1.95–1.60 (m, 4H), 1.61 (s, 6H), 1.40 (9H, s) ppm.

(v) (2S,3S)-3-[5-(3-Cyano-1,1-dimethyl-2-propynyl)-2-methoxybenzyl]amino-2-phenylpiperidine Dihydrochloride (Compound 66)

This compound was prepared from Compound 65 in the same manner of Compound 57.

mp 218°–219° C. IR (KBr) 3450, 2930, 2655, 2265, 1559, 1505, 1452, 1414, 1256, 1027 cm$^{-1}$. $^1$H-NMR (270 MHz) (free base; CDCl$_3$) 7.35–7.20 (m, 5H), 7.19 (dd, 1H, J=8.4, 2.6 Hz), 7.05 (d, 1H, J=2.6 Hz), 6.66 (d, 1H, J=8.4 Hz), 3.91 (d, 1H, J=2.2 Hz), 3.65 (d, 1H, J=13.9 Hz), 3.50 (s, 3H), 3.40 (d, 1H, J=13.9 Hz), 3.33–3.23 (m, 1H), 2.88–2.74 (m, 2H), 2.20–2.08 (m, 1H), 2.04–1.82 (m, 1H), 1.80–1.55 (m, 1H), 1.58 (s, 6H) 1.50–1.40 (s, 1H) ppm.

Example 15

Preparation of (2S,3S)-3-[5-(3-phenyl-1,1-dimethyl-2-propynyl)-2-methoxybenzyl]amino-2-phenylpiperidine Dihydrochloride (Compound 70)

(i) 4-(3-Phenyl-1,1-dimethyl-2-propynyl)anisole (Compound 67)

To a stirred solution of Compound 21 (299 mg, 1.72 mmol), PhI (385 mg, 1.89 mmol), and (PPh$_3$)$_2$PdCl$_2$ (60 mg, 0.086 mmol) in Et₂NH (10 ml) was added CuI (33 mg, 0.17 mmol) at r.t. under N₂, and stirred for 18 h. The mixture was quenched by the addition of H₂O, and extracted with Et₂O. The combined organic layers were washed with brine, dried over MgSO₄, filtered, and concentrated. This was purified by SiO₂ chromatography to give Compound 67 (360 mg, 84%) as a colorless oil.

¹H-NMR (270 MHz) (CDCl₃) 7.53 (d, 2H, J=8.8 Hz), 7.48–7.42 (m, 2H), 7.36–7.25 (m, 3H), 6.88 (d, 2H, J=8.8 Hz), 3.81 (s, 3H), 1.66 (6H, s) ppm.

(ii) 5-(3-Phenyl-1,1-dimethyl-2-propynyl)-2-methoxybenzaldehyde (Compound 68)

This compound was prepared from Compound 67 in the same manner of Compound 2.

¹H-NMR (270 MHz) (CDCl₃) 10.48 (s, 1H), 8.02 (d, 1H, J=2.9 Hz), 7.89 (dd, 1H, J=8.8, 2.9 Hz), 7.47–7.40 (m, 2H), 7.35–7.26 (m, 3H), 6.98 (d, 1H, J=8.8 Hz), 3.92 (s, 3H), 1.67 (s, 6H) ppm.

(iii) (2S,3S)-1-tert-Butoxycarbonyl-3-[5-(3-phenyl-1,1-dimethyl-2-propynyl)-2-methoxybenzyl]amino-2-phenylpiperidine (Compound 69)

This compound was prepared from Compound 68 and Compound 17 in the same manner of Compound 18.

¹H-NMR (270 MHz) (CDCl₃) 7.65–7.22 (m, 12H), 6.77 (d, 1H, J=8.4 Hz), 5.52–5.40 (m, 1H), 4.00–3.90 (m, 1H), 3.84 (s, 2H), 3.70 (s, 3H), 3.13–2.94 (m, 2H), 1.95–1.50 (m, 4H), 1.64 (s, 3H), 1.63 (s, 3H), 1.40 (9H, s) ppm.

(iv) (2S,3S)-3-[5-(3-Phenyl-1,1-dimethyl-2-propynyl)-2-methoxybenzyl]amino-2-phenylpiperidine Dihydrochloride (Compound 70)

This compound was prepared from Compound 69 in the same manner of Compound 57.

mp 222°–224° C. IR (KBr) 3430, 2970, 2935, 2660, 2365, 1560, 1505, 1454, 1418, 1254, 1023 cm⁻¹. ¹H-NMR (270 MHz) (free base; CDCl₃) 7.48–7.20 (m, 12H), 6.66 (d, 1H, J=8.4 Hz), 4.04 (d, 1H, J=1.6 Hz), 3.86 (d, 1H, J=13.9 Hz), 3.55 (d, 1H, J=13.9 Hz), 3.54–3.40 (m, 1H), 3.41 (s, 3H), 2.96–2.82 (m, 2H), 2.40–2.15 (m, 2H), 1.80–1.50 (m, 2H), 1.61 (s, 6H) ppm.

Example 16

Preparation of (2S, 3S)-3-(5-cyanomethyl-2-methoxybenzyl)amino-2-phenylpiperidine Dihydrochloride (Compound 73)

(i) 5-Cyanomethyl-2-methoxybenzyaldehyde (Compound 71)

This compound was prepared from 4-methoxyphenylacetnitrile in the same manner of Compound 2.

¹H-NMR (270 MHz) (CDCl₃) 10.46 (s, 1H), 8.75 (d, 1H, J=2.2 Hz), 7.56 (dd, 1H, J=8.8, 2.2 Hz), 7.03 (d, 1H, J=8.8 Hz), 3.96 (s, 3H), 3.73 (s, 2H) ppm.

(ii) (2S,3S)-1-tert-Butoxycarbonyl-3-(5-cyanomethyl-2-methoxybenzyl)amino-2-phenylpiperidine (Compound 72)

This compound was prepared from Compound 71 and Compound 17 in the same manner of Compound 18.

¹H-NMR (270 MHz) (CDCl₃) 7.62–7.54 (m, 2H), 7.36–7.15 (m, 5H), 6.79 (d, 1H, J=8.4 Hz), 5.52–5.43 (m, 1H), 3.98–3.73 (m, 3H), 3.71 (s, 3H), 3.65 (s, 2H), 3.12–2.90 (m, 2H), 1.93–1.40 (m, 4H), 1.41 (9H, s) ppm.

(iii) (2S,3S)-3-(5-Cyanomethyl-2-methoxybenzyl)amino-2-phenylpiperidine Dihydrochloride (Compound 73)

This compound was prepared from Compound 72 in the same manner of Compound 57.

mp 215°–217° C. IR (KBr) 3430, 2935, 2665, 2250, 1558, 1504, 1452, 1417, 1333, 1252, 1032 cm⁻¹. ¹H-NMR (270 MHz) (free base; CDCl₃) 7.40–7.22 (m, 5H), 7.12 (dd, 1H, J=8.4, 2.2 Hz), 6.91 (d, 1H, J=2.2 Hz), 6.68 (d, 1H, J=8.4 Hz), 4.00–3.95 (m, 1H), 3.75–3.35 (m, 3H), 3.58 (s, 2H), 3.50 (s, 3H), 2.93–2.78 (m, 2H), 2.20–1.50 (m, 4H) ppm.

Example 17

Preparation of (2S,3S)-3-[5-(2-propynyl)-2-methoxybenzyl|amino-2-phenylpiperidine Dihydrochloride (Compound 79)

(i) 4-Methoxyphenylacetaldehyde (Compound 74)

This compound was prepared from 4-methoxyphenylacetnitrile in the same manner of Compound 45.

¹H-NMR (270 MHz) (CDCl₃) 9.72 (t, 1H, J=2.6 Hz), 7.13 (d, 2H, J=8.8 Hz), 6.91 (d, 2H, J=8.8 Hz), 3.81 (s, 3H), 3.63 (d, 2H, J=2.6 Hz) ppm.

(ii) 4-(3,3-Dibromo-2-propenyl)anisole (Compound 75)

This compound was prepared from Compound 74 in the same manner of Compound 53.

¹H-NMR (270 MHz) (CDCl₃) 7.11 (d, 2H, J=8.4 Hz), 6.84 (d, 2H, J=8.4 Hz), 6.54 (t, 1H, J=7.3 Hz), 3.79 (s, 3H), 3.37 (d, 2H, J=7.3 Hz) ppm.

(iii) 4-(2-Propynyl)anisole (Compound 76)

To a stirred solution of Compound 75 (478 mg, 1.56 mmol) in THF (6 ml) was added n-BuLi (1.94 ml, 3.28 mmol), at −78° C. under N₂, then warmed up to 0° C., and stirred for 5 h. The mixture was quenched by the addition of NH₄Cl aq., and extracted with Et₂O. The combined organic layers were dried over MgSO₄, filtered, and concentrated. This was purified by SiO₂ chromatography to give Compound 76 (213 mg, 94%) as a colorless oil.

¹H-NMR (270 MHz) (CDCl₃) 7.26 (d, 2H, J=8.8 Hz), 6.86 (d, 2H, J=8.8 Hz), 3.80 (s, 3H), 3.55 (d, 2H, J=2.6 Hz), 2.15 (t, 1H, J=2.6 Hz) ppm.

(iv) 5-(2-Propynyl)-2-methoxybenzaldehyde (Compound 77)

This compound was prepared from Compound 76 in the same manner of Compound 2.

¹H-NMR (270 MHz) (CDCl₃) 10.45 (s, 1H), 7.79 (d, 1H, J=2.2 Hz), 7.56 (dd, 1H, J=8.4, 2.2 Hz), 6.97 (d, 1H,J=8.4 Hz), 3.93 (s, 3H), 3.57 (d, 2H, J=2.6 Hz), 2.20 (t, 1H, J=2.6 Hz) ppm.

(v) (2S,3S)-1-tert-Butoxycarbonyl-3-[5-(2-propynyl)-2-methoxybenzyl|amino-2-phenylpiperidine (Compound 78)

This compound was prepared from Compound 77 and Compound 17 in the same manner of Compound 18.

¹H-NMR (270 MHz) (CDCl₃) 7.63–7.54 (m, 2H), 7.37–7.13 (m, 5H), 6.75 (d, 1H, J=8.4 Hz), 5.52–5.42 (m, 1H), 4.00–3.90 (m, 1H), 3.89–3.75 (m, 2H), 3.69 (s, 3H), 3.51 (d, 2H, J=2.2 Hz), 3.13–2.90 (m, 2H), 2.15 (t, 1H, J=2.2 Hz), 1.90–1.45 (m, 4H), 1.40 (9H, s) ppm.

(vi) (2S,3S)-3-|5-(2-Propynyl)-2-methoxybenzyl| amino-2-phenylpiperidine Dihydrochloride (Compound 79)

This compound was prepared from Compound 78 in the same manner of Compound 57.

mp 219°–221° C. IR (KBr) 3450, 3180, 2935, 2650, 2365, 1556, 1504, 1450, 1412, 1332, 1250, 1034 cm⁻¹. ¹H-NMR (270 MHz) (free base; CDCl₃) 7.40–7.22 (m, 5H), 7.20–7.12 (m, 1H), 6.92 (d, 1H, J=2.2 Hz), 6.64 (d, 1H, J=8.4 Hz), 3.95 (d, 1H, J=2.2 Hz), 3.74 (d, 1H, J=13.9 Hz), 3.52–3.30 (m, 2H), 3.47 (d, 2H, J=2.6 Hz), 3.43 (s, 3H), 2.90–2.76 (m, 2H), 2.23–1.95 (m, 2H), 2.16 (t, 1H, J=2.6 Hz), 1.90–1.40 (s, 2H) ppm.

Example 18

Preparation of (2S,3S)-3-|2-Methoxy-5-[1-(1,3-dithiolan-2-yl)-1-methylethyl|benzyl]amino-2-phenylpiperidine Dihydrochloride (Compound 83)

(i) 4-|1-Methyl-1-(1,3-dithiolan-2-yl)ethyl]anisole (Compound 80)

To a mixture of BF₃-2AcOH (526 mg, 2.8 mmol) and ethandithiol (527 mg, 5.6 mmol) in CH₂Cl₂ (10 ml) was added a solution of Compound 45 (500 mg, 2.8 mmol) in CH₂Cl₂ (5 ml) at room temperature. The mixture was stirred at same temperature for 30 min. and to this was added to water. The mixture was extracted with CH₂Cl₂. The combined extracts were washed with NaHCO₃ solution and brine, then this was dried (MgSO₄) and concentrated in vacuo to give crude product. The crude product was purified by a column chromatography to give Compound 80 (680 mg) as an oil.

¹H-NMR (CDCl₃) 7.35 (d, J=9 Hz, 2H), 6.85 (d, J=9 Hz, 2H), 4.91 (s, 1H), 3.80 (s, 3H), 3.1–2.9 (m, 4H), 1.47 (s, 6H)

(ii) 2-Methoxy-5-[1-(1,3-dithiolan-2-yl)-1-methylethyl]benzaldehyde (Compound 81)

To a stirred solution of Compound 80 (0.254 g, 1 mmol) in dry CH₂Cl₂ (5 ml) was added a solution of TiCl₄ in CH₂Cl₂ (1M, 3 ml) with cooling (−60° C.). After 3 min., to this was added dichloromethyl methyl ether (0.46 g, 4 mmol) dropwise. The reaction mixture was stirred at same temperature for 1 hr. The mixture was poured into water and stirred at room temperature for 15 min. The organic layer was separated and the aqueous layer was extracted with Et₂O (50 ml×2). The combined solution was washed with brine, dried (MgSO₄) and concentrated in vacuo to give crude product. The crude product was purified by a column chromatography to give Compound 81 (86 mg) as an oil ¹H-NMR (CDCl₃) 10.46 (s, 1H), 7.90 (d, J=3 Hz, 1H), 7.65 (dd, J=9 Hz, 3 Hz, 1H), 6.94 (d, J=9 Hz, 1H), 4.88 (s, 1H), 3.92 (s, 3H), 2.9–3.1 (m, 4H), 1.49 (s, 6H)

(iii) (2S,3S)-1-tert-Butoxycarbonyl-3-|2-Methoxy-5-|1-(1,3-dithiolan-2-yl)-1-methylethyl|benzyl|amino-2-phenylpiperidine (Compound 82)

This compound was prepared from Compound 81 and Compound 17 in the same manner of Compound 18.

¹H-NMR (CDCl₃) 7.60–7.57 (m, 2H), 7.35–7.2 (m, 5H), 6.75 (d, J=8 Hz, 1H), 5.45 (br, 1H), 4.89 (s, 1H), 3.95 (m, 1H), 3.82 (s, 2H), 3.70 (s, 3H), 3.1–2.9 (m, 4H), 1.8–1.2 (m, 8H), 1.5 (s, 6H), 1.40 (s, 9H)

(iv) (2S,3S)-3-|2-Methoxy-5-|1-(1,3-dithiolan-2-yl)-1-methylethyl|benzyl|amino-2-phenylpiperidine Dihydrochloride (Compound 83)

To a solution of Compound 82 (0.128 g) in EtOAc (5 ml) was added an excess amount of 10% HCl-MeOH (1 ml) for 8 hr. The resulting precipitate was collected and washed with EtOAc to give Compound 83 (0.069 g) as a colorless crystal.

¹H-NMR(free base, CDCl₃) 7.35–7.2 (m, 6H), 7.07 (d, J=2 Hz, 1H), 6.62 (d, J=8 Hz, 1H), 4.86 (s, 1H), 4.01 (s, 1H), 3.93 (d, J=14 Hz, 1H), 3.55 (d, J=14 Hz, 1H), 3.5–3.4 (1H), 3.39 (s, 3H), 3.1–2.9 (m, 4H), 2.9–2.8 (m, 2H), 2.2–1.2 (4H), 1.42 (s, 6H)

mp 254°–257° C.

Example 19

Preparation of (2S,3S)-3-(2-Methoxy-5-(2-methyl-3-oxo-butan-2-yl)-benzyl)amino-2-phenylpiperidine Dihydrochloride (Compound 87)

(i) 3-(4-Methoxyphenyl)-3-methylbutan-2-one (Compound 84)

This compound was prepared according to the procedures described in J. Amer. Chem. Soc., Vol. 80, p. 4556, 1958.

(ii) 5-(2-Methyl-3-oxo-butan-2-yl)-2-methoxybenzaldehyde (Compound 85)

This compound was prepared from Compound 84 in the same manner of Compound 81.

¹H-NMR (CDCl₃) 10.48 (s, 1H), 7.81 (d, J=3 Hz, 1H), 7.40 (dd, J=9 Hz, 3 Hz, 1H), 6.98 (d, J=9 Hz, 1H), 3.94 (s, 3H), 1.93 (s, 3H), 1.49 (s, 6H).

(iii) (2S,3S)-1-tert-Butoxycarbonyl-3-|2-Methoxy-5-(2-methyl-3-oxo-butan-2-yl)-benzyl)|amino-2-phenylpiperidine (Compound 86)

This compound was prepared from Compound 85 and Compound 17 in the same manner of Compound 18.

¹H-NMR (CDCl₃) 7.58–7.56 (m, 2H), 7.35–7.2 (m, 3H), 7.11 (d, J=3 Hz, 1H), 7.07 (dd, J=8 Hz, 3 Hz, 1H), 6.77 (d, J=8 Hz, 1H), 5.46 (br, 1H), 4.0–3.9 (br, 1H), 3.81 (s, 2H), 3.70 (s, 3H), 3.1–3.0 (m, 2H), 1.92 (s, 3H), 1.9–1.3 (m, 5H), 1.44 (s, 6H), 1.40 (s, 9H)

(iv) (²S,3S)-3-(2-Methoxy-5-(2-methyl-3-oxo-butan-2-yl)-benzyl)amino-2-phenylpiperidine Dihydrochloride (Compound 87)

This compound was prepared from Compound 86 in the same manner of Compound 83.

¹H-NMR(free base, CDCl₃) 7.35–7.20 (m, 5H), 7.02 (dd, J=8 Hz, 3 Hz, 1H), 6.90 (d, J=3 Hz, 1H), 6.64 (d, J=8 Hz, 1H), 3.88 (d, J=2 Hz, 1H), 3.65 (d, J=14 Hz, 1H), 3.46 (s, 3H), 3.35 (d, J=14 Hz, 1H), 3.28–3.25 (1H), 2.9–2.7 (m, 2H), 2.2–1.8 (m, 2H), 1.88 (s, 3H), 1.7–1.5 (1H), 1.40 (s, 6H)

mp 260°–264° C.

Example 20

Preparation of (2S,3S)-3-(5-(1-Cyano-4-oxa-cyclohexyl)-2-methoxybenzyl)amino-2-phenylpiperidine Dihydrochloride (Compound 91)

(i) 4-(1-Cyano-4-oxa-cyclohexyl)anisole (Compound 88)

To a solution of 4-methoxyphenylacetonitrile (5 g, 34 mmol) and NaH (2.8 g, 71 mmol) in DMSO (50 ml) was added 2-chloroethyl ether (5.3 g, 37 mmol) with cooling. The mixture was stirred at room temperature for 3 h, quenched with water, and extracted with CH₂Cl₂. The combined extracts were dried (Na₂SO₄) and concentrated in vacuo to give an oil which was purified by a column chromatography to give Compound 88 (5.3 g, 24 mmol, 71%) as a colorless oil.

¹H-NMR (CDCl₃) 7.46–6.90 (m, 3H), 4.13–3.79 (m, 4H), 3.82 (s, 3H), 2.18–2.00 (m, 4H)

(ii) 5-(1-Cyano-4-oxa-cyclohexyl)-2-methoxybenzaldehyde (Compound 89)

This compound was prepared from Compound 88 in the same manner of Compound 2.

¹H-NMR (CDCl₃) 10.47 (s, 1H), 7.92–7.03 (m, 3H), 4.16–3.83 (m, 4H), 3.97 (s, 3H), 2.20–2.00 (m, 4H)

(iii) (2S,3S)-1-tert-Butoxycarbonyl-3-(5-(1-cyano-4-oxa-cyclohexyl)-2-methoxybenzyl)amino-2-phenylpiperidine (Compound 90)

This compound was prepared from Compound 89 and Compound 17 in the same manner of Compound 18.

¹H-NMR (CDCl₃) 7.62–6.80 (m, 8H), 5.47 (br, 1H), 4.15–3.80 (m, 8H), 3.72 (s, 3H), 3.24–2.96 (m, 2H), 2.20–1.50 (m, 8H), 1.40+1.36 (s, 9H)

(iv) (2S,3S)-3-(5-(1-Cyano-4-oxa-cyclohexyl)-2-methoxybenzyl)amino-2-phenylpiperidine Dihydrochloride (Compound 91)

This compound was prepared from Compound 90 in the same manner of Compound 83.

¹H-NMR(free base, CDCl₃) 7.38–6.64 (m, 8H), 4.14–2.76 (m, 11H), 3.52 (s, 3H), 2.20–1.40 (m, 8H)
mp 269°–274° C.

Example 21

Preparation of (2S,3S)-3-(5-(1-Cyano-2,2,2-trifluoro-1-methylethyl)-2-methoxybenzyl)amino-2-phenylpiperidine Dihydrochloride (Compound 95)

(i) 3,3,3-Trifluoro-2-(4-methoxyphenyl)-2-methylpropionitrile (Compound 92)

This compound was prepared according to the procedures described in the Japanese Unexamined Publication No. 62234034.

(ii) 5-(1-Cyano-2,2,2-trifluoro-1-methylethyl)-2-methoxybenzaldehyde(Compound 93)

This compound was prepared from Compound 92 in the same manner of Compound 2.

¹H-NMR (CDCl₃) 10.47 (s, 1H), 8.00–7.10 (m, 3H), 3.99 (s, 3H), 2.02 (s, 3H)

(iii) (2S,3S)-1-tert-Butoxycarbonyl-3-(5-(1-cyano-2,2,2-trifluoro-1-methylethyl)-2-methoxybenzyl)amino-2-phenylpiperidine (Compound 94)

This compound was prepared from Compound 93 and Compound 17 in the same manner of Compound 18.

¹H-NMR (CDCl₃) 7.60–6.80 (m, 8H), 5.50 (br, 1H), 4.02–2.95 (m, 6H), 3.90 (s, 3H), 2.10–1.40 (m, 4H), 2.07 (s, 3H), 1.39 (s, 9H)

(iv) (2S,3S)-3-(5-(1-Cyano-2,2,2-trifluoro-1-methylethyl)-2-methoxybenzyl)amino-2-phenylpiperidine Dihydrochloride (Compound 95)

This compound was prepared from Compound 94 in the same manner of Compound 83.

¹H-NMR(free base, CDCl₃) 7.43–6.70 (m, 8H), 3.92–2.73 (m, 6H), 3.53 (s, 3H), 2.18–1.40 (m, 4H), 1.90 (s, 3H)

mp 285°–290° C.

TABLE

| EX.-# | Ar | R¹ | X |
|---|---|---|---|
| 1 | phenyl | cyclopropyl-CN | methoxy |
| 2 | phenyl | cyclopropyl-N(C=O)- | methoxy |
| 3 | phenyl | isopropyl-CN | methoxy |
| 4 | phenyl | tert-butyl-C≡CH | methoxy |
| 5 | phenyl | tert-butyl-CN | methoxy |
| 6 | phenyl | -CH(CH₃)C(=O)O- | methoxy |
| 7 | phenyl | -C(CN)₂CH₃ | methoxy |
| 8 | phenyl | tert-butyl-CN | isopropoxy |
| 9 | phenyl | -C(CH₃)₂CH₂CN | methoxy |
| 10 | phenyl | cyclohexyl-CN | methoxy |
| 11 | phenyl | cyclopentyl-CN | methoxy |
| 12 | phenyl | tert-butyl-C≡CH | methoxy |

TABLE-continued (I)

![structure showing piperidine with NH, Ar, and benzyl-NH-CH2-phenyl with R1 and X substituents]

| EX.-# | Ar | R¹ | X |
|---|---|---|---|
| 13 | phenyl | —C(CH3)2—C≡C—CO2CH3 | methoxy |
| 14 | phenyl | —C(CH3)2—C≡C—CN | methoxy |
| 15 | phenyl | —C(CH3)2—C≡C—phenyl | methoxy |
| 16 | phenyl | cyclopropyl-CN | methoxy |
| 17 | phenyl | —CH2—C≡CH | methoxy |
| 18 | phenyl | —C(CH3)2—(dithiolane) | methoxy |
| 19 | phenyl | —C(CH3)2—C(=O)—CH3 | methoxy |
| 20 | phenyl | tetrahydropyranyl-CN | methoxy |
| 21 | phenyl | —C(CF3)—CN | methoxy |

*X is at 2-position of the benzene ring.
**The stereochemistry of 2-aryl and 3-benzylamino is (2S, 3S).

We claim:
1. A compound of the general formula:

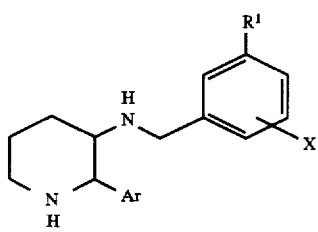

(I)

and its pharmaceutically acceptable salts, wherein $R^1$ is $(C_1-C_4)$alkyl, $(C_3-C_6)$cycloalkyl, halo$(C_1-C_4)$alkyl or tetrahydropyranyl having one or more substitutents selected from cyano, $COR^2$ or $C\equiv CR^6$ wherein $R^2$ is hydrogen or $(C_1-C_4)$alkyl and $R^6$ is hydrogen, halo, cyano, $(C_1-C_6)$alkyl, COOH, COO$(C_1-C_4)$alkyl or phenyl;

X is $(C_1-C_6)$alkoxy or halo $(C_1-C_6)$alkoxy; and

Ar is phenyl optionally substituted with halo.

2. A compound according to claim 1, wherein $R^1$ is $C_1-C_4$ alkyl, cyclopropyl or halo $C_1-C_4$ alkyl, substituted with cyano, $C\equiv CH$ or $COCH_3$.

3. A compound according to claim 1, wherein X is methoxy.

4. A compound according to claim 1 selected from
(2S,3S)-3-(5-(1-cyanocyclopropyl)-2-methoxybenzyl)amino-2-phenylpiperidine dihydrochloride or its salts;
(2S,3S)-3-(5-(1-cyanoethyl)-2-methoxybenzyl)amino-2-phenyl-1-piperidine or its salts;
(2S,3S)-3-(2-methoxy-5-(1,1-dimethyl-2-propynyl)benzyl)amino-2-phenylpiperidine or its salts;
(2S,3S)-3-(5-(1-cyano-1-methylethyl)-2-methoxybenzyl)amino-2-phenylpiperidine or its salts;
(2S,3S)-3-(5-(1,1-dicyanoethyl)-2-methoxybenzyl)amino-2-phenylpiperidine or its salts;
(2S,3S)-3-(5-(1-cyano-1-methylethyl)-2-isopropoxybenzyl)amino-2-phenylpiperidine or its salts;
(2S,3S)-3-(5-(2-cyano-1,1-dimethylethyl)-2-methoxybenzyl)amino-2-phenylpiperidine or its salts;
(2S,3S)-3-(5-cyanomethyl-2-methoxybenzyl)amino-2-phenylpiperidine or its salts;
(2S,3S)-3-[5-(2-propynyl)-2-methoxybenzyl]amino-2-phenylpiperidine or its salts;
(2S,3S)-3-(2-methoxy-5-(2-methyl-3-oxo-butan-2-yl)-benzyl)amino-2-phenylpiperidine or its salts; and
(2S,3S)-3-(5-(1-cyano-2,2,2-trifluoro-1-methylethyl)-2-methoxybenzyl)amino-2-phenylpiperidine or its salts.

5. A pharmaceutical composition for preventing or treating a medical condition selected from allergic disorders, angiogenesis, gastrointestinal disorders, centra nervous system disorders, inflammatory diseases, emesis, urinary incontinence, pain, migraine, and sunburn for which antagonist activity toward substance P is needed, in a mammalian subject, comprises a substance P antagonistic effective amount of a compound of claim 1.

6. A method of preventing or treating a medical condition selected from allergic disorders, angiogenesis, gastrointestinal disorders, centra nervous system disorders, inflammatory diseases, emesis, urinary incontinence, pain, migraine, and sunburn for which antagonist activity toward substance P is needed, in a mammalian subject, comprises administering to said subject a substance P antagonistic effective amount of a compound of claim 1.

7. A pharmaceutical composition for preventing or treating symptoms or adverse conditions caused by *Helicobacter pylori* in a mammalian subject comprises a therapeutically effective amount of a compound of claim 1.

8. A method of preventing or treating symptoms or adverse conditions caused by *Helicobacter pylori* in a mammalian subject comprises administering to said subject a therapeutically effective amount of a compound of claim 1.

* * * * *